(12) United States Patent
Bae et al.

(10) Patent No.: US 11,996,500 B2
(45) Date of Patent: May 28, 2024

(54) LED LIGHTING APPARATUS HAVING ADDITIONAL FUNCTION

(71) Applicant: SEOUL VIOSYS CO., LTD., Ansan-si (KR)

(72) Inventors: Hee Ho Bae, Ansan-si (KR); Yeong Min Yoon, Ansan-si (KR); A Young Lee, Ansan-si (KR)

(73) Assignee: Seoul Viosys Co., Ltd., Ansan-si (KR)

(*) Notice: Subject to any disclaimer, the term of this patent is extended or adjusted under 35 U.S.C. 154(b) by 474 days.

(21) Appl. No.: 16/726,622

(22) Filed: Dec. 24, 2019

(65) Prior Publication Data
US 2020/0212265 A1 Jul. 2, 2020

Related U.S. Application Data

(60) Provisional application No. 62/792,865, filed on Jan. 15, 2019, provisional application No. 62/784,885, filed on Dec. 26, 2018.

(51) Int. Cl.
*H01L 27/15* (2006.01)
*H01L 33/50* (2010.01)

(52) U.S. Cl.
CPC .......... *H01L 33/504* (2013.01); *H01L 27/153* (2013.01)

(58) Field of Classification Search
CPC . H01L 33/504; H01L 25/0753; H01L 27/153; H01L 33/502; A61N 5/0624; A61N 5/0613; A61N 2005/0636; A61N 2005/0662; A61N 2005/0661; A61N 2005/0651

(Continued)

(56) References Cited

U.S. PATENT DOCUMENTS 8,567,973 B2 10/2013 Li et al.
10,441,809 B2 10/2019 Van Bommel et al.
(Continued)

FOREIGN PATENT DOCUMENTS

JP 2008-034833 2/2008
JP 2008-508918 3/2008
(Continued)

OTHER PUBLICATIONS

Extended European Search Report dated Aug. 19, 2022, for European Patent Application No. 19905053.5.
(Continued)

*Primary Examiner* — Hrayr A Sayadian
(74) *Attorney, Agent, or Firm* — Oblon, McClelland, Maier & Neustadt, L.L.P.

(57) ABSTRACT

A lighting apparatus including at least two of first, second, and third light units, in which the first light unit includes a first LED emitting light having a peak wavelength in a range of 286 to 304 nm and a first wavelength converter, and to emit a portion of light from the first LED to the outside, the second light unit includes a second LED emitting light having a peak wavelength in a range of 400 to 420 nm and a second wavelength converter, and to emit a portion of light from the second LED to the outside, and the third light unit includes a third LED emitting light having a peak wavelength in a range of 286 to 470 nm and a third wavelength converter emitting light having a central wavelength in a range of 685 to 705 nm, 790 to 840 nm, or 875 to 935 nm.

14 Claims, 15 Drawing Sheets

(58) Field of Classification Search
USPC .................................. 257/415, 13, 79, 88, 89
See application file for complete search history.

(56) References Cited

U.S. PATENT DOCUMENTS

| | | | |
|---|---|---|---|
| 10,679,975 | B2 | 6/2020 | Hikmet et al. |
| 10,753,577 | B2 | 8/2020 | Van Bommel et al. |
| 11,213,693 | B2 * | 1/2022 | Lee .................. A61N 5/0613 |
| 2009/0054953 | A1 | 2/2009 | Whitehurst |
| 2012/0098460 | A1 | 4/2012 | Miyasaka et al. |
| 2013/0279149 | A1 | 10/2013 | Udatsu et al. |
| 2015/0014715 | A1 | 1/2015 | Hsing Chen et al. |
| 2018/0209609 | A1 | 7/2018 | Hikmet et al. |
| 2018/0358514 | A1 | 12/2018 | Tragl et al. |

FOREIGN PATENT DOCUMENTS

| | | |
|---|---|---|
| JP | 2015-523875 | 8/2015 |
| JP | 2018-518046 | 7/2018 |
| JP | 2018-524783 | 8/2018 |
| JP | 2018-200884 | 12/2018 |
| KR | 10-2011-0003198 | 1/2011 |
| KR | 10-2012-0031182 | 3/2012 |
| KR | 10-2012-0120996 | 11/2012 |
| KR | 10-2017-0120772 | 11/2017 |
| WO | 2009114390 | 9/2009 |
| WO | 2013150413 | 10/2013 |
| WO | 2017080807 | 5/2017 |
| WO | 2017125322 | 7/2017 |
| WO | 2018091433 | 5/2018 |

OTHER PUBLICATIONS

Office Action issued from the Japanese Patent Office dated Oct. 17, 2023 for Japanese Patent Application No. 2021-537170 (with English Translation).

* cited by examiner

LED LIGHTING APPARATUS HAVING ADDITIONAL FUNCTION

CROSS-REFERENCE TO RELATED APPLICATIONS

This application claims priority from and the benefit of U.S. Provisional Application Nos. 62/784,885, filed on Dec. 26, 2018, and 62/792,865, filed on Jan. 15, 2019, which are hereby incorporated by reference for all purposes as if fully set forth herein.

BACKGROUND

Field

Exemplary embodiments relate to a lighting apparatus using an LED, and more particularly, to an LED lighting apparatus having an additional function.

Discussion of the Background

As an inorganic light source, light emitting diodes have been used in various fields including displays, vehicular lamps, general lighting, and the like. In particular, with various advantages of light emitting diodes, such as longer lifespan, lower power consumption, and quicker response than existing light sources, light emitting diodes have been replacing existing light sources.

Meanwhile, sunlight exhibits a broad spectrum of wavelengths in the ultraviolet, visible, and infrared regions. The human body is adapted to sunlight, and has utilized light of a wide wavelength range over a broad wavelength range of sunlight.

Unlike sunlight, general lighting is limited to the visible region and cannot provide light in a wavelength range other than visible light. As such, ordinary people living under an illumination light source cannot absorb light of a wavelength that is known to be beneficial to the human body other than visible light.

The above information disclosed in this Background section is only for understanding of the background of the inventive concepts, and, therefore, it may contain information that does not constitute prior art.

SUMMARY

Lighting apparatus, light emitting diode packages, and lighting systems constructed according to exemplary embodiments of the invention have an additional function, in addition to a lighting function providing visible light.

Exemplary embodiments also provide an energy-efficient lighting apparatus, a light emitting diode package, and a lighting system, in addition to providing visible light, similar to sunlight.

Exemplary embodiments further provide a lighting apparatus having an additional function by using unit light sources having a simple structure.

Additional features of the inventive concepts will be set forth in the description which follows, and in part will be apparent from the description, or may be learned by practice of the inventive concepts.

A light emitting apparatus according to an exemplary embodiment includes at least one light emitting unit including a single light emitting diode and a wavelength converter for converting a wavelength of light emitted from the light emitting diode, in which the light emitting unit emits white light, and further emits at least one of light suitable for producing vitamin D, light suitable for sterilizing an pathogenic microorganism, and light suitable for producing a cell activating substance.

A light emitting apparatus according to another exemplary embodiment includes at least two or more of a first light emitting unit, a second light emitting unit, and a third light emitting unit, in which the first light emitting unit includes a first light emitting diode configured to emit light having a peak wavelength in a range of about 286 nm to about 304 nm and a first wavelength converter, and configured to emit a portion of light generated by the first light emitting diode to the outside, the second light emitting unit includes a second light emitting diode configured to emit light having a peak wavelength in a range of about 400 nm to about 420 nm and a second wavelength converter, and configured to emit a portion of light generated by the second light emitting diode to the outside, the third light emitting unit includes a third light emitting diode configured to emit light having a peak wavelength in a range of about 286 nm to about 470 nm and a third wavelength converter including a wavelength conversion substance configured to emit light having a central wavelength in a range of about 685 nm to about 705 nm, about 790 nm to about 840 nm, or about 875 nm to about 935 nm.

A light emitting apparatus according to further exemplary embodiment includes a first light emitting diode having a peak wavelength in a range of about 300 nm to about 470 nm, a second light emitting diode emitting ultraviolet light having a peak wavelength in a range of about 286 nm to about 304 nm, and a wavelength converter for converting a wavelength of light emitted from the first light emitting diode, in which the lighting apparatus is configured to emit white light and light that causes production of vitamin D and a cell activating substance in a human body.

A light emitting apparatus according to still another exemplary embodiment includes a first light emitting diode having a peak wavelength in a range of about 300 nm to about 470 nm, a second light emitting diode emitting ultraviolet light having a peak wavelength in a range of about 286 nm to about 304 nm, a third light emitting diode having a peak wavelength in a range of about 685 nm to about 705 nm, about 790 nm to about 840 nm, or about 875 nm to about 935 nm, and a wavelength converter for converting a wavelength of light emitted from the first light emitting diode, in which white light is emitted by a combination of the first light emitting diode and the wavelength converter, and light generated by the second and third light emitting diodes is emitted to the outside.

A light emitting diode package according to yet another exemplary embodiment includes a first light emitting diode having a peak wavelength in a range of about 300 nm to about 470 nm, a second light emitting diode emitting ultraviolet light having a peak wavelength in a range of about 286 nm to about 304 nm, and a wavelength converter for converting a wavelength of light emitted from the first light emitting diode, in which the light emitting diode package emits white light, and emits light suitable for producing vitamin D and light suitable for producing a cell activating substance.

A light emitting diode package according to further yet exemplary embodiment includes a first light emitting diode having a peak wavelength in a range of about 300 nm to about 470 nm, a second light emitting diode emitting ultraviolet light having a peak wavelength in a range of about 286 nm to about 304 nm, and a third light emitting diode having a peak wavelength in a range of about 685 nm to about 705 nm, about 790 nm to about 840 nm, or about 875 nm to about 935 nm, and a wavelength converter for converting a wavelength of light emitted from the first light emitting diode, in which white light is emitted by a combination of the first light emitting diode and the wavelength converter, and light generated by the second and third light emitting diodes is emitted to the outside.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concepts.

DETAILED DESCRIPTION

Figure 1:
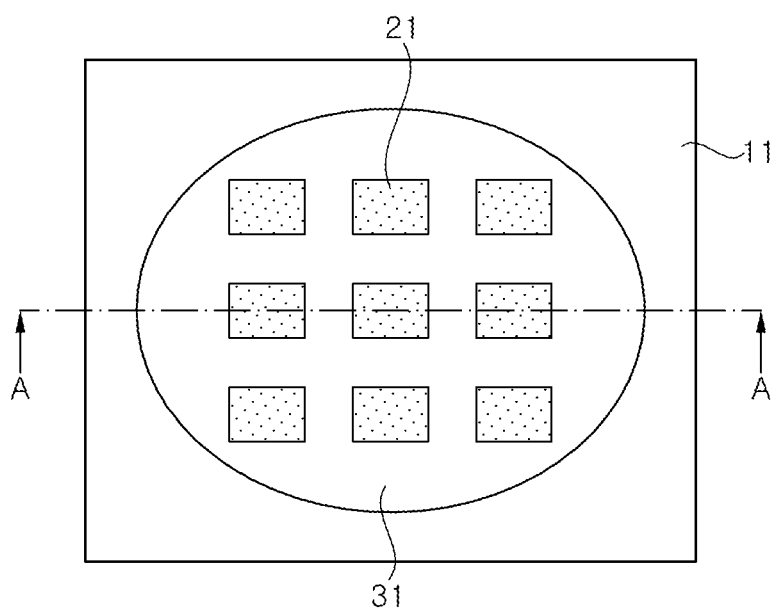
FIG. 1 is a schematic plan view of a lighting apparatus according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

A lighting apparatus according to an exemplary embodiment includes at least one light emitting unit including a single light emitting diode and a wavelength converter for converting a wavelength of light emitted from the light emitting diode, in which the light emitting unit emits white light, and emits light suitable for producing vitamin D, light suitable for sterilizing an pathogenic microorganism, or light suitable for producing a cell activating substance.

The single light emitting diode may be used to emit white light and emit ultraviolet light necessary for the synthesis of vitamin D, thereby providing the lighting apparatus having an additional function without having a complicated structure.

The light emitting diode may emit ultraviolet light having a peak wavelength in a range of about 286 nm to about 304 nm. More specifically, the light emitting diode may emit ultraviolet light having a peak wavelength in a range of about 291 nm to about 301 nm. Ultraviolet light in this range may effectively synthesize vitamin D.

In some exemplary embodiments, the wavelength converter may include a blue phosphor, a green phosphor, and a red phosphor. White light may be implemented using the phosphors.

In an exemplary embodiment, the light emitting diode may emit visible light having a peak wavelength in a range of about 400 nm to about 420 nm, and the wavelength converter may include a blue phosphor, a green phosphor, and a red phosphor. The light emitting diode may emit visible light having relatively short wavelength, and thus, a spectrum of visible region similar to sunlight may be implemented.

The cell activating substance may be nitric oxide (NO) produced by cytochrome c oxidase activity in mitochondria. NO improves the health of the human body by affecting pain relief and improving blood circulation.

Further, light of the second light emitting diode absorbed by the intracellular mitochondria may causes the mitochondria to produce more ATPs and enhance metabolism.

The wavelength converter may emit light having a central wavelength in a range of about 685 nm to about 705 nm, about 790 nm to about 840 nm, or about 875 nm to about 935 nm. In these wavelength ranges, an energy absorption rate of cytochrome c oxidase is relatively higher. In particular, the cytochrome c oxidase exhibits the highest absorption in the range of 790 nm to 840 nm, and followed by in the range of 875 nm to 935 nm. Accordingly, the wavelength converter may emit light having the central wavelength at least in the range of 790 nm to 840 nm or in the range of 875 nm to 935 nm. The wavelength conversion substance may include a phosphor or a quantum dot. The quantum dot has a particularly narrow half width, and thus, it is suitable for producing the cell activating substance.

Irradiance of light emitted from the wavelength conversion substance having the central wavelength in the range of about 685 nm to about 705 nm, about 790 nm to about 840 nm, or about 875 nm to about 935 nm may be 570 W/m² or less.

In another exemplary embodiment, the light emitting diode may emit ultraviolet light in a range of about 286 nm to about 304 nm, or visible light in a range of 400 nm to 420 nm.

The lighting apparatus may further include a circuit board, on which the light emitting unit is mounted. A plurality of light emitting units may be mounted on the circuit board, and the light emitting units may be connected to one another in series, in parallel, or in reverse-parallel.

In some exemplary embodiments, the at least one light emitting unit may include at least two different light emitting units, in which the different light emitting units may emit white light, respectively, and emit different light, either light suitable for producing vitamin D, light suitable for sterilizing an pathogenic microorganism, or light suitable for producing a cell activating substance.

In another exemplary embodiment, the at least one light emitting unit may include at least three different light emitting units, in which the different light emitting units may emit white light, respectively, and emit light suitable for producing vitamin D, light suitable for sterilizing an pathogenic microorganism, or light suitable for producing a cell activating substance.

A lighting apparatus according to another exemplary embodiment includes at least two or more of a first light emitting unit, a second light emitting unit, and a third light emitting unit, in which the first light emitting unit includes a first light emitting diode emitting light having a peak wavelength in a range of about 286 nm to about 304 nm and a first wavelength converter, and emits a portion of light generated by the first light emitting diode to the outside, the second light emitting unit includes a second light emitting diode emitting light having a peak wavelength in a range of about 400 nm to about 420 nm and a second wavelength converter, and emits a portion of light generated by the second light emitting diode to the outside, the third light emitting unit includes a third light emitting diode emitting light having a peak wavelength in a range of about 286 nm to about 470 nm and a third wavelength converter, and the third wavelength converter includes a wavelength conversion substance having a central wavelength in a range of about 685 nm to about 705 nm, about 790 nm to about 840 nm, or about 875 nm to about 935 nm.

The wavelength conversion substance having the central wavelength in the range of about 685 nm to about 705 nm, about 790 nm to about 840 nm, or about 875 nm to about 935 nm may be a quantum dot. The quantum dot has a narrow half width, and thus, can emit converted light in high intensity, thereby being suitable for emitting light of a specific wavelength.

Each of the first wavelength converter and the second wavelength converter may include a blue phosphor, a green phosphor, and a red phosphor, and the third wavelength converter may further include a green phosphor and a red phosphor.

The first light emitting unit, the second light emitting unit, and the third light emitting unit may be driven independently of one another.

The first light emitting unit, the second light emitting unit and the third light emitting unit may emit white light, respectively.

In some exemplary embodiments, the third light emitting diode may emit light having the peak wavelength in the range of about 400 nm to about 420 nm.

A lighting apparatus according to another exemplary embodiment includes a first light emitting diode having a peak wavelength in a range of about 300 nm to about 470 nm, a second light emitting diode emitting ultraviolet light having a peak wavelength in a range of about 286 nm to about 304 nm, and a wavelength converter for converting a wavelength of light emitted from the first light emitting diode, in which the lighting apparatus emits white light, and emits light suitable for producing vitamin D and light suitable for producing a cell activating substance.

The lighting apparatus according to an exemplary embodiment may implement white light and emit light suitable for generating ultraviolet light and a cell activating substance necessary for vitamin D production, thereby providing beneficial light to the human body similar to sunlight. Furthermore, since the lighting apparatus emits light by using the light emitting diode, it may emit light even in an ultraviolet region, which is insufficient in sunlight, and may emit light more suitable for vitamin D production than sunlight.

The white light may be implemented by the first light emitting diode and the wavelength converter. Further, the first light emitting diode may have a peak wavelength in a range of about 400 nm to about 420 nm.

The wavelength converter may include a blue phosphor, in which the white light may have a peak by the first light emitting diode and a peak by the blue phosphor, and the peak by the first light emitting diode and the peak by the blue phosphor may be located at different wavelengths from each other.

In some exemplary embodiments, the lighting apparatus may have a plurality of light emitting units spaced apart from one another, in which each light emitting unit includes a first light emitting diode and a wavelength converter covering the first light emitting diode.

Furthermore, the light emitting units may implement white light having the same or different color temperatures.

In another exemplary embodiment, white light may be implemented by a combination of the light emitting units.

According to an exemplary embodiment, the wavelength converter may include a blue phosphor, a green phosphor, and a red phosphor. In another exemplary embodiment, the wavelength converter may include a green phosphor and a red phosphor, or may include an orange phosphor, without the blue phosphor.

The second light emitting diode may emit light suitable for vitamin D synthesis. In particular, the second light emitting diode may emit ultraviolet light having a peak wavelength in a range of about 291 nm to about 301 nm. Ultraviolet light in this range may effectively synthesize vitamin D.

In an exemplary embodiment, the second light emitting diode may be spaced apart from the wavelength converter. Light emitted from the second light emitting diode may be prevented from entering the wavelength converter, and thus, light emitted from the second light emitting diode may be prevented from being wavelength converted. Accordingly, light loss due to the wavelength conversion of light emitted from the second light emitting diode may be prevented, and, furthermore, the color temperature of the lighting apparatus may be easily adjusted.

The cell activating substance may be nitric oxide (NO) produced by cytochrome c oxidase activity in mitochondria. NO improves the health of the human body by affecting pain relief and improving blood circulation. Furthermore, light suitable for producing the cell activating substance is absorbed by the intracellular mitochondria, and thus, allows the mitochondria to produce more ATPs and enhances metabolism.

In an exemplary embodiment, the wavelength converter may include a wavelength converting substance converting a wavelength into light having a peak wavelength in a range of about 685 nm to about 705 nm, about 790 nm to about 840 nm, or about 875 nm to about 935 nm.

The wavelength converter may emit light having a peak wavelength in a range of about 685 nm to about 705 nm, about 790 nm to about 840 nm, or about 875 nm to about 935 nm. In these wavelength ranges, an energy absorption rate of cytochrome c oxidase is relatively higher. In particular, the cytochrome c oxidase exhibits the highest absorption in the range of 790 nm to 840 nm, and followed by in the range of 875 nm to 935 nm. Accordingly, the wavelength converter may have the peak wavelength at least in the range of 790 nm to 840 nm, or in the range of 875 nm to 935 nm. The wavelength converting substance may include a phosphor or a quantum dot. The quantum dot has a particularly narrow half width, and thus, it is suitable for producing the cell activating substance.

In another exemplary embodiment, the lighting apparatus may further include a third light emitting diode, in which the third light emitting diode emits light having a peak wavelength in a range of about 685 nm to about 705 nm, about 790 nm to about 840 nm, or about 875 nm to about 935 nm.

Irradiance of light emitted from the wavelength converting substance having light having the peak wavelength in the range of about 685 nm to about 705 nm, about 790 nm to about 840 nm, or about 875 nm to about 935 nm may be 570 $W/m^2$ or less.

In one exemplary embodiment, light generated by the first light emitting diode may be emitted to the outside of the lighting apparatus to sterilize pathogenic microorganisms.

In another exemplary embodiment, the lighting apparatus may further include a fourth light emitting diode emitting light suitable for sterilizing pathogenic microorganisms. The fourth light emitting diode may be spaced apart from the wavelength converter.

The fourth light emitting diode may have a peak wavelength in a range of about 400 nm to about 420 nm, and may further have a peak wavelength of about 400 nm to about 410 nm, and even further, a peak wavelength of about 405 nm.

The lighting apparatus may further include a circuit board, on which the first to third light emitting diodes are mounted.

A lighting apparatus according to another exemplary embodiment includes a first light emitting diode having a peak wavelength in a range of about 300 nm to about 470 nm, a second light emitting diode emitting ultraviolet light having a peak wavelength in a range of about 286 nm to about 304 nm, a third light emitting diode having a peak wavelength in a range of about 685 nm to about 705 nm, about 790 nm to about 840 nm, or about 875 nm to about 935 nm, and a wavelength converter for converting a wavelength of light emitted from the first light emitting diode, in which white light is emitted by a combination of the first light emitting diode and the wavelength converter, and light generated by the second and third light emitting diodes is emitted to the outside.

The second and third light emitting diodes may be included together with the first light emitting diode, and thus, it may help the human body to synthesize vitamin D and generate the cell activating substance.

The lighting apparatus may further include a fourth light emitting diode spaced apart from the wavelength converter and having a peak wavelength in a range of about 400 nm to about 420 nm. Light generated by the fourth light emitting diode may be used to sterilize pathogenic microorganisms.

A light emitting diode package according to another exemplary embodiment includes a first light emitting diode having a peak wavelength in a range of about 300 nm to about 470 nm, a second light emitting diode emitting ultraviolet light having a peak wavelength in a range of about 286 nm to about 304 nm, and a wavelength converter for converting a wavelength of light emitted from the first light emitting diode, in which the light emitting diode package emits white light, and emits light suitable for producing vitamin D and light suitable for producing a cell activating substance.

A light emitting diode package according to another exemplary embodiment includes a first light emitting diode having a peak wavelength in a range of about 300 nm to about 470 nm, a second light emitting diode emitting ultraviolet light having a peak wavelength in a range of about 286 nm to about 304 nm, and a third light emitting diode having a peak wavelength in a range of about 685 nm to about 705 nm, about 790 nm to about 840 nm, or about 875 nm to about 935 nm, and a wavelength converter for converting a wavelength of light emitted from the first light emitting diode, in which white light is emitted by a combination of the first light emitting diode and the wavelength converter, and light generated by the second and third light emitting diodes is emitted to the outside.

Hereinafter, exemplary embodiments of the invention will be described in detail with reference to the accompanying drawings.

Figure 2:
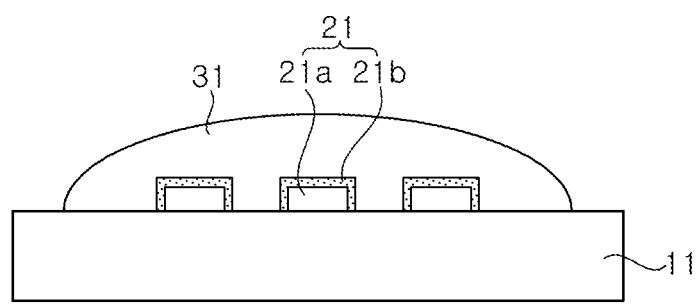
FIG. 2 is a schematic cross-sectional view taken along line A-A of FIG. 1.

FIG. 1 is a schematic plan view of a lighting apparatus according to an exemplary embodiment, and FIG. 2 is a schematic cross-sectional view taken along line A-A of FIG. 1.

Referring to FIG. 1 and FIG. 2, the lighting apparatus may include a circuit board 11, at least one light emitting unit 21, and a molding member 31.

The circuit board 11 may have a circuit pattern for supplying power to the light emitting units 21. The circuit board 11 may be a printed circuit board, for example, a metal-PCB. The circuit board 11, on which the light emitting unit 21 is mounted, may be disposed in the lighting apparatus as a light emitting module.

At least one first light emitting unit 21 is mounted on the circuit board 11 as a unit light source for implementing white light. A plurality of first light emitting diodes 21 may be electrically connected to one another in various ways, for example, in series, in parallel or in series/parallel.

The light emitting unit 21 includes a light emitting diode 21a and a wavelength converter 21b. According to an exemplary embodiment, the light emitting diode 21a may emit ultraviolet light of UVB. For example, the light emitting diode 21a may emit light having a central wavelength in a range of about 286 nm to about 304 nm, more specifically, in a range of about 291 nm to about 301 nm. When ultraviolet light in this range is irradiated to the human body, vitamin D may be efficiently synthesized. The light emitting diode 21a may be an inorganic light emitting diode, which may be formed using a group III nitride semiconductor, without being limited thereto. The light emitting diode chip may have a flip chip type, a vertical type, or a horizontal type structure, without being limited thereto.

The wavelength converter 21b converts a wavelength of light emitted from the light emitting diode 21a. The wavelength converter 21b may cover the light emitting diode 21a. In particular, when light emitting diodes 21a are formed in plural, the wavelength converters 21b may cover the light emitting diodes 21a, respectively. However, the inventive concepts are not limited thereto, and the light emitting diodes 21a may be covered together by one wavelength converter 21b. For example, the molding member 31 may include a wavelength conversion substance to cover the light emitting diodes 21a.

The wavelength converter 21b includes a wavelength conversion substance to convert the wavelength of light generated by the light emitting diode 21a to implement white light. According to an exemplary embodiment, the wavelength converter 21b may include a blue phosphor, a green phosphor and a red phosphor. According to another exemplary embodiment, the wavelength converter 21b may include a blue phosphor and an orange phosphor. In some exemplary embodiments, the wavelength converter may include a quantum dot, instead of or in addition to the phosphor. The wavelength converter 21a may have a structure, for example, in which phosphors or quantum dots are dispersed in a silicone resin or glass.

The blue phosphor may be a BAM-based, a halo-phosphate-based, or an aluminate-based phosphor, and may include, for example, $BaMgAl_{10}O_{17}:Mn^{2+}$, $BaMgAl_{12}O_{19}:Mn^{2+}$ or $(Sr,Ca,Ba)PO_4Cl:Eu^{2+}$. The blue phosphor may have, for example, a peak wavelength in a range of 440 nm to 500 nm.

The green phosphor may include $LuAG(Lu_3(Al,Gd)_5O_{12}:Ce^{3+})$, $YAG(Y_3(Al,Gd)_5O_{12}:Ce^{3+})$, $Ga-LuAG((Lu,Ga)_3(Al,Gd)_5O_{12}:Ce^{3+})$, $Ga-YAG ((Ga,Y)_3(Al,Gd)_5O_{12}:Ce^{3+})$, $LuYAG ((Lu,Y)_3(Al,Gd)_5O_{12}:Ce^{3+})$, ortho-silicate $((Sr,Ba,Ca,Mg)_2SiO_4:Eu^{2+})$, oxynitride $((Ba,Sr,Ca)Si_2O_2N_2:Eu^{2+})$, $\beta$-SiAlON:$Eu^{2+}$, Ca-$\alpha$-SiAlON:$Eu^{2-}$, or thio gallate $(SrGa_2S_4:Eu^{2+})$. The green phosphor may have a peak wavelength in a range of 500 nm to 600 nm.

The red phosphor may be a nitride-based, a sulfide-based, a Fluoride or an oxynitride-based phosphor, and, specifically, may include $CASN(CaAlSiN_3:Eu^{2+})$, $(Ba,Sr,Ca)_2Si_5N_8:Eu^{2+}$, $(Ca,Sr)S_2:Eu^{2+}$, or $(Sr,Ca)_2SiS_4:Eu^{2+}$. The red phosphor may have a peak wavelength in a range of 600 nm to 700 nm.

White light may be implemented by a combination of the light emitting diode 21a and the wavelength converter 21b. Most of ultraviolet light emitted from the light emitting diodes 21a may be wavelength-converted by the wavelength converter 21a, and some ultraviolet light may be emitted to the outside without wavelength conversion. Since ultraviolet light is not observed with the naked eye, light that has been wavelength-converted into visible light by the wavelength converter 21b and emitted to the outside may be observed. Thus, a spectrum of visible light emitted from the lighting apparatus is determined by the combination of wavelength converting substances in the wavelength converter 21b. As compared to white light emitted from conventional blue light emitting diode, white light emitted by the wavelength conversion substance according to an exemplary embodiment may prevent the occurrence of eye diseases or skin diseases caused by the blue wavelength. This will be described in more detail below with reference to FIG. 4 and FIG. 5.

The molding member 31 may cover the light emitting units 21. The molding member 31 may protect the light emitting units 21 from an external environment. The molding member 31 may be formed of, for example, a transparent resin, such as silicone resin, or transparent glass. In some exemplary embodiments, the molding member 31 may include a wavelength conversion substance.

Ultraviolet light generated in the light emitting diode 21a and emitted to the outside may be used for the synthesis of vitamin D. 7-dehydrocholesterol in skin cells is known to react with UVB to synthesize cholecalciferol (vitamin D3).

Figure 3:
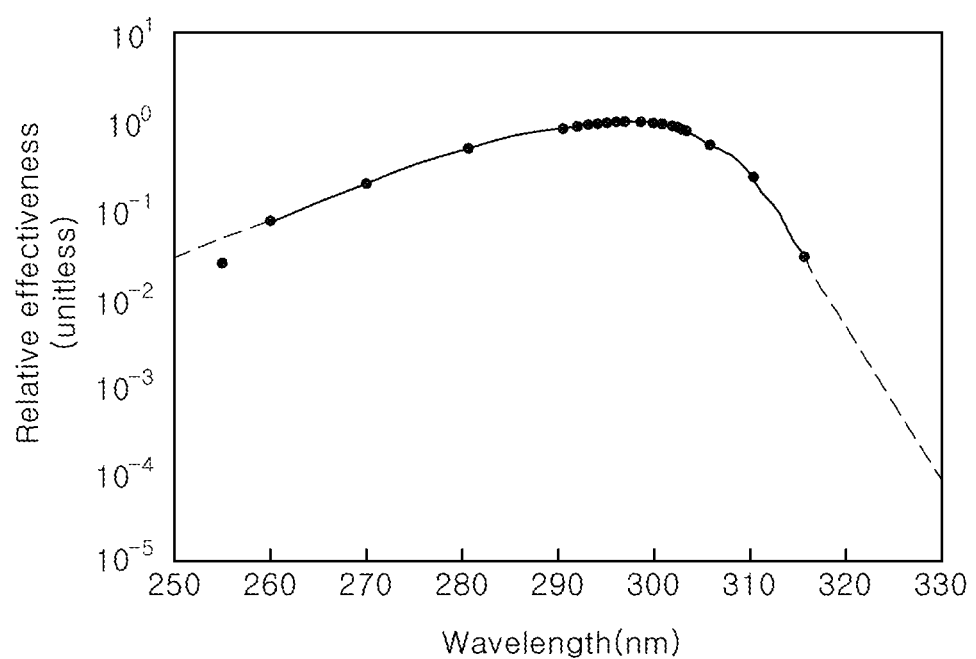
FIG. 3 is a graph showing effectiveness of vitamin D production in the human body according to wavelengths.

FIG. 3 is a graph showing effectiveness of vitamin D production in the human body according to wavelengths, which was published in CIE 174: 2006.

Referring to FIG. 3, ultraviolet light of about 298 nm is most efficient for vitamin D production, and that in a range of about 291 nm to about 301 nm exhibits an efficiency of about 90% or more of the highest efficiency. Ultraviolet light in a range of about 286 nm to about 304 nm exhibits at least about 70% efficiency of the highest efficiency, and that in a range of 281 nm to 306 nm exhibits at least about 50% efficiency of the highest efficiency. When a peak wavelength of the light emitting diode 21a is about 298 nm, it is the most efficient for vitamin D production, and, within the range of about 286 nm to about 304 nm, it will exhibit a relatively favorable efficiency of 70% or more for vitamin D production.

Vitamin D is involved in calcium metabolism, and a deficiency of vitamin D may cause a major impediment to bone growth. A recommended daily dose of vitamin D, which is generally suggested to maintain an adequate level of vitamin D, varies from country to country, generally in a range of about 400 IU to about 800 IU, and has been adjusted upward. For example, the International Commission on Illumination (CIE) suggests the required UVB exposure to produce 1000 IU of vitamin D, which is about 21-34 $J/m^2$ for the entire body of the second skin type based on the sunlight at noon in midsummer. Meanwhile, a reference dose for the human exposure safety range for UVB provided by the American Conference of Governmental Industrial Hygienists (ACGIH) is 47 $J/m^2$ for 290 nm, about 65 $J/m^2$ for 297 nm, and 100 $J/m^2$ for 300 nm.

As such, a dose of UVB irradiated by the lighting apparatus may need to be adjusted, such that the UVB dosage may be used for vitamin D synthesis while not exceeding the safety range. In addition, since the daily permissible reference dose increases as the wavelength increases in the ultraviolet region of UVB, the light emitting diode 21a having a peak wavelength of about 298 nm or longer, for example, about 298 nm to about 301 nm, may emit a greater amount of ultraviolet light, thereby making the lighting apparatus more suitable for the vitamin D synthesis function.

Figure 4:
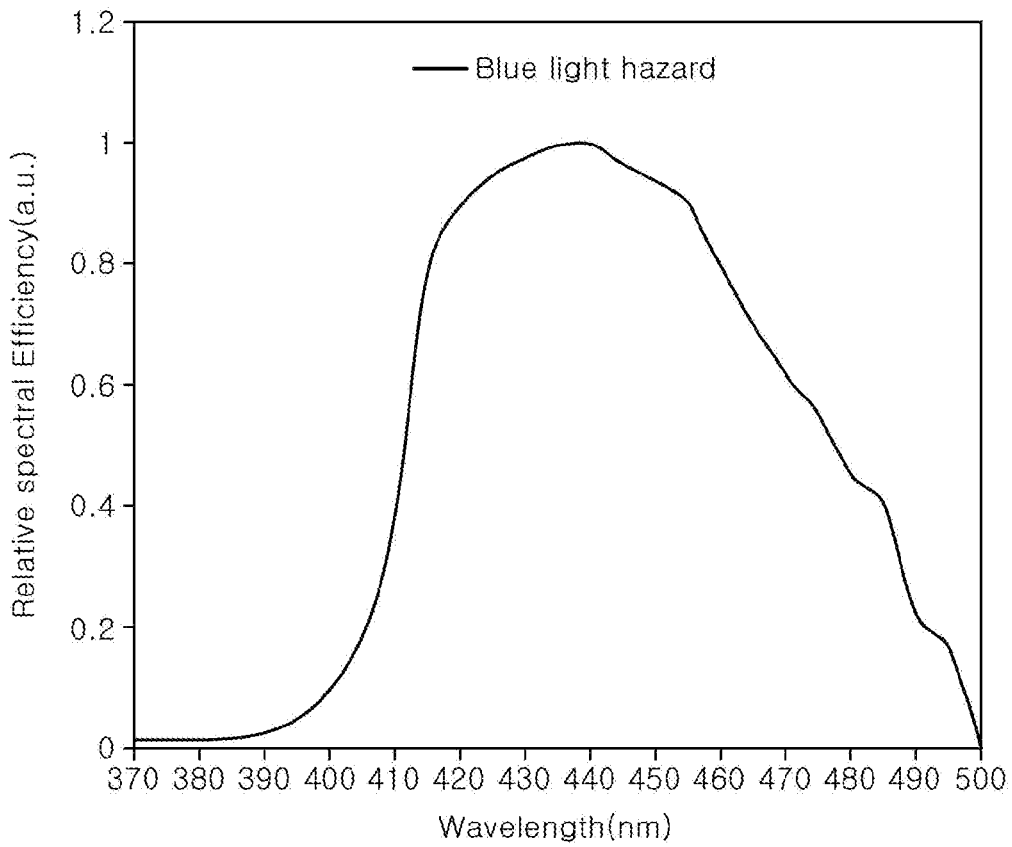
FIG. 4 is a graph showing a degree of hazard according to wavelengths of blue light.

FIG. 4 is a graph showing a degree of hazard according to wavelengths of blue light.

Blue light is generally known to cause eye diseases and skin diseases. In particular, blue light exhibits the highest degree of hazard between 430 nm and 440 nm. A wavelength range of 420 nm to 455 nm exhibits 90% or more degree of hazard based on the highest hazard value, a wavelength range of 413 nm to 465 nm exhibits 70% or more degree of hazard, and a wavelength range of 411 nm to 476 nm exhibits 50% or more degree of hazard.

Figure 5:
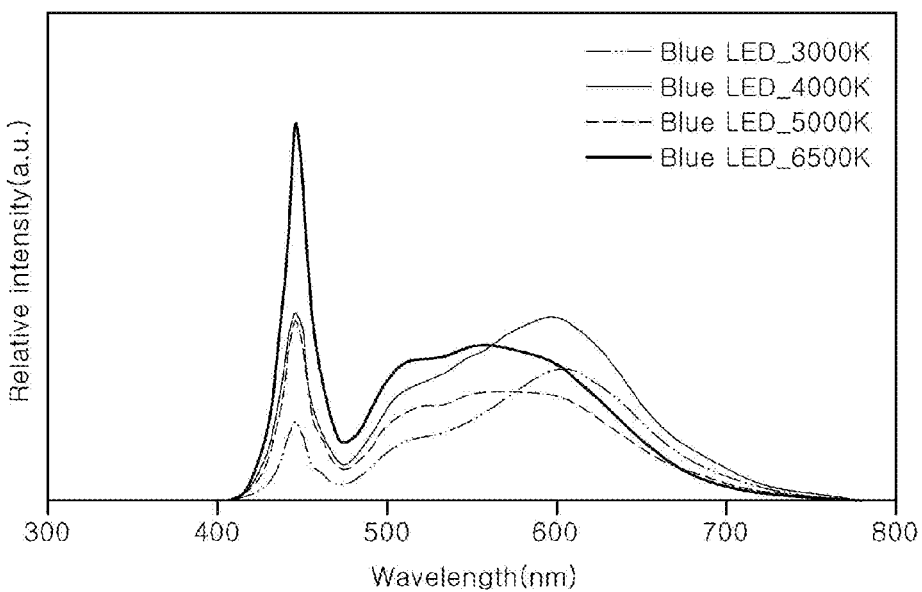
FIG. 5 is a graph showing a spectrum of a white light source using a blue light emitting diode.

FIG. 5 shows a spectrum of a conventional white light source using a blue light emitting diode.

Referring to FIG. 5, a conventional white light source implements white light using a yellow phosphor, or a green phosphor and a red phosphor together with a blue light emitting diode. A type and an amount of phosphor are controlled according to a desired color temperature, and an intensity of the blue light may be increased as the color temperature increases.

A blue light emitting diode used in the conventional white light source generally has a central wavelength (e.g., peak wavelength) in a range of 430 nm to 470 nm. Blue light in this range has a relatively high degree of hazard as shown in FIG. 4. In addition, light emitted from the blue light emitting diode is mixed with light emitted from the phosphor to implement white light. As such, as the desired color temperature of the white light source increases, the intensity of the blue light may be increased, thereby increasing the hazard of causing eye diseases or skin diseases.

Since the light emitting diode according to an exemplary embodiment, as shown in FIG. 1 and FIG. 2, uses the light emitting diode emitting ultraviolet light, light emitted from the light emitting diode 21a may not be used to implement white light. In particular, light in the visible region is implemented by light emitted from the wavelength converter 21b. Accordingly, the spectrum of the visible region of light emitted from the lighting apparatus according to an exemplary embodiment may have a similar intensity throughout the entire visible region, as similar to sunlight. In this manner, light of a specific wavelength, such as light in the blue region, may not need to have an abnormally higher intensity than light in other regions as that in the conventional white light source. Accordingly, the lighting apparatus according to an exemplary embodiment may significantly reduce the hazard to the human body.

Figure 6:
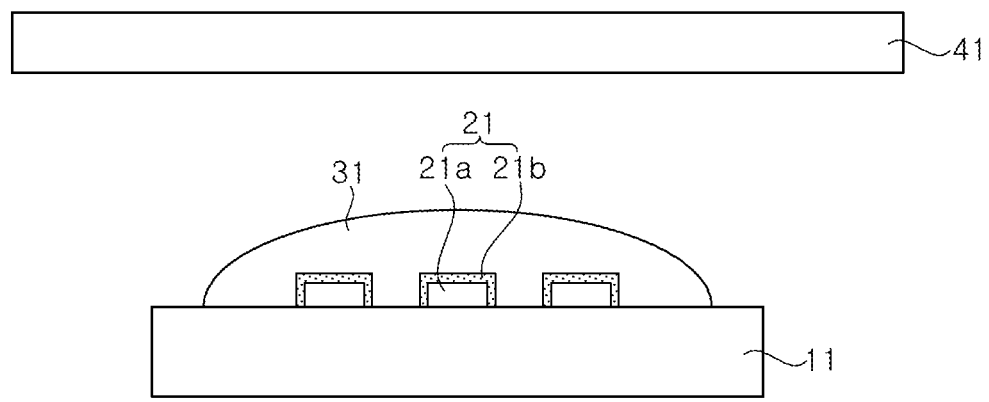
FIG. 6 is a schematic cross-sectional view of a lighting apparatus according to another exemplary embodiment.

FIG. 6 is a schematic cross-sectional view of a lighting apparatus according to another exemplary embodiment.

Referring to FIG. 6, the lighting apparatus according to the illustrated exemplary embodiment is generally similar to that described with reference to FIG. 1 and FIG. 2, except for a filter 41.

The filter 41 may block unnecessary ultraviolet light emitted from the light emitting units 21 from being emitted to the outside. For example, the filter 41 may block light in a range of about 301 nm to about 400 nm to prevent harmful effects on the human body caused by ultraviolet light in this range. Light in the above range may be emitted by, for example, a wavelength conversion substance. As such, the filter 41 is disposed outside of the wavelength converter 21b. The filter 41 may be disposed in the molding member 31, or may be disposed the outside of the molding member 31 as shown in FIG. 6. The filter 41 may include a band pass filter, for example.

Although the light emitting unit 21 has been described as including the light emitting diode 21a and the wavelength converter 21b covering the light emitting diode 21a in the illustrated exemplary embodiment, however, the inventive concepts are not limited thereto. For example, in some exemplary embodiments, the light emitting unit 21 may be provided in a package form.

Figure 7:
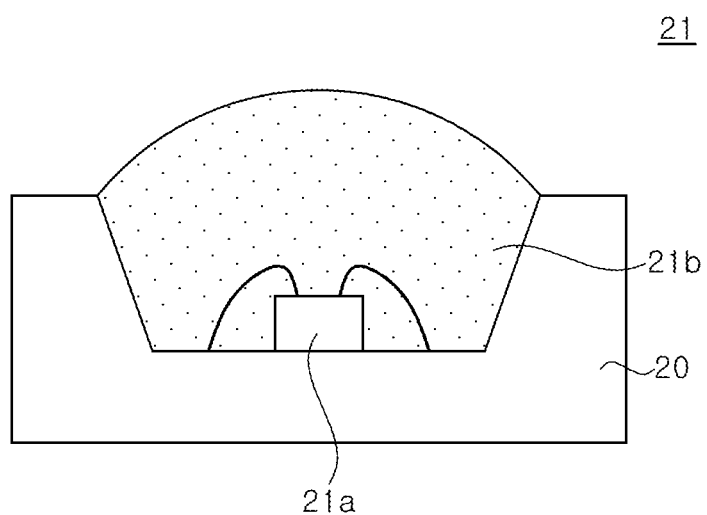
FIG. 7 is a schematic cross-sectional view of a light emitting unit according to another exemplary embodiment.

FIG. 7 is a schematic cross-sectional view of a light emitting unit according to another exemplary embodiment. The light emitting device illustrated in FIG. 7 may be provided in a conventional package form.

Referring to FIG. 7, the first light emitting unit 21 includes a first light emitting diode 21a and a first wavelength converter 21b. The first light emitting diode 21a may be mounted in a cavity of a housing 20, and the first wavelength converter 21b covers the light emitting diode 21a disposed in the cavity. The first light emitting diode 21a may be electrically connected to lead electrodes through bonding wires.

The package shown in FIG. 7 may be formed as various other kinds of packages. In addition, the first wavelength converter 21b may cover the light emitting diode 21a in various shapes. In some exemplary embodiments, when the light emitting units 21 are provided in the package form, the molding member 31 may be omitted.

Figure 8:
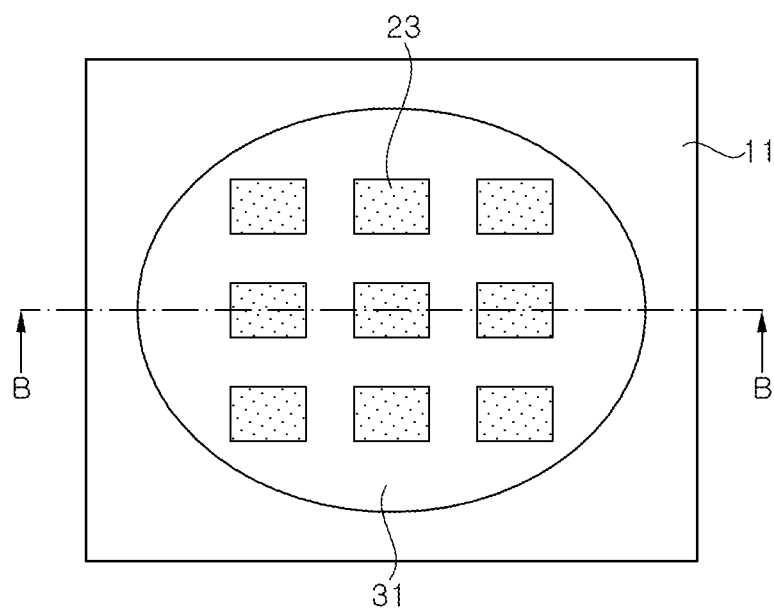
FIG. 8 is a schematic plan view of a lighting apparatus according to another exemplary embodiment.
Figure 9:
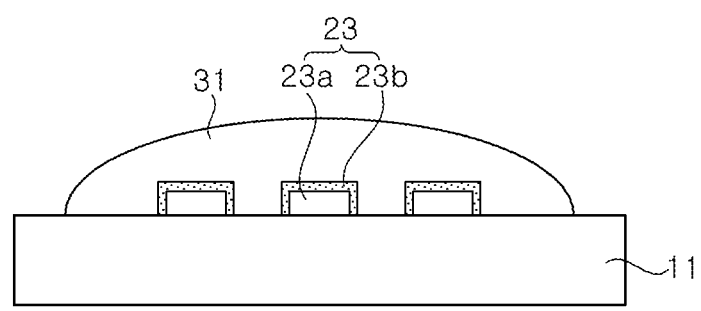
FIG. 9 is a schematic cross-sectional view taken along line B-B of FIG. 8.

FIG. 8 is a schematic plan view of a lighting apparatus according to another exemplary embodiment, and FIG. 9 is a schematic cross-sectional view taken along line B-B of FIG. 8.

Referring to FIG. 8 and FIG. 9, the lighting apparatus according to the illustrated exemplary embodiment is generally similar to that described with reference to FIG. 1 and FIG. 2, except that light emitting units 23 include light emitting diodes 23a emitting short-wavelength visible light of violet, instead of the ultraviolet light emitting diodes 21a.

More particularly, the light emitting diode 23a has a peak wavelength in a range of about 400 nm to about 420 nm, and light of the wavelength in this range is suitable for sterilizing pathogenic microorganisms. In particular, the light emitting diode 23a may emit light having a peak wavelength of about 400 nm to about 410 nm, and more particularly, a peak wavelength of about 405 nm. The wavelength of about 405 nm is absorbed by porphyrin, a substance existing in the cells of bacteria, which may then generate reactive oxygens, and the reactive oxygens may be accumulated and destroy cell walls. As such, the wavelength in the visible range of the above range is suitable for sterilizing pathogenic microorganisms without causing eye diseases or skin diseases. As used herein, sterilization may refer to killing or damaging a pathogenic microorganism to reduce or hinder the growth of the pathogenic microorganism.

A wavelength converter 23b may include a wavelength conversion substance for converting light of the light emitting diode 23a into blue, green, and red light. In another exemplary embodiment, the wavelength converter 23b may include blue and orange wavelength converting substances for converting light of the light emitting diode 23a into blue and orange light. Since the type of the wavelength conversion substance is substantially similar to that described above with reference to FIG. 1 and FIG. 2, detailed descriptions thereof will be omitted to avoid redundancy.

A portion of light generated by the light emitting diode 23a is converted into long wavelength visible light by the wavelength conversion substance, and some of light is emitted to the outside of the lighting apparatus without wavelength conversion. Light generated by the light emitting diode 23a and emitted to the outside is mixed with light converted by the wavelength conversion substance to produce white light, as well as providing sterilizing function.

To enhance the sterilizing function, irradiance of light of the wavelength generated by the light emitting diode 23a and emitted to the outside may be greater than that of the wavelength-converted light in the wavelength conversion substance. However, the inventive concepts are not limited thereto. For example, in some exemplary embodiments, as described above with reference to FIG. 4, to reduce the hazard of light having the wavelength in the blue region, the irradiance of light generated by the light emitting diode 23a and emitted to the outside may be less than that of the wavelength-converted light in the wavelength conversion substance.

Figure 10:
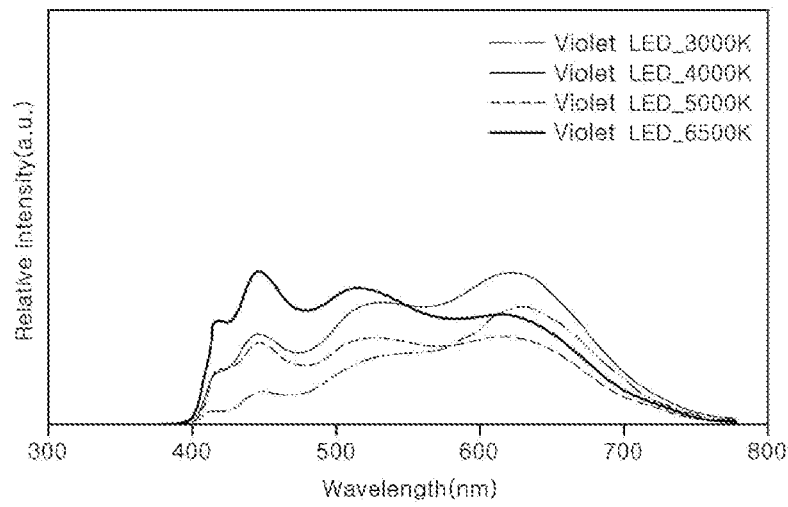
FIG. 10 is a graph showing representative spectra of a lighting apparatus according to exemplary embodiments.

FIG. 10 is a graph showing spectra of white light of various color temperatures implemented by a combination of the light emitting diode 23a and the wavelength converter 23b.

Referring to FIG. 10, white light of each color temperature is implemented by a combination of light emitted from the first light emitting diode 23a and light emitted from the phosphors. In addition, irradiance of light emitted from the first light emitting diode 23a at each color temperature may be less than that of light emitted from the blue phosphor. As the color temperature increases, although the irradiance of light emitted from the first light emitting diode 23a may be increased, irradiance of blue light emitted from the blue phosphor may be increased at a greater extent. In addition, the irradiance of light emitted from the first light emitting diode 23a may be less than that of light emitted from the green phosphor, and may be less than that of light emitted from the red phosphor.

Accordingly, the lighting apparatus according to the illustrated exemplary embodiment may further prevent the occurrence of eye diseases or skin diseases caused by light emitted from the light emitting diodes 23a. However, as described above, since the wavelength in the 400 nm to 420 nm range has a relatively low hazard to the human body, the irradiance thereof may be further increased.

According to the exemplary embodiments, the violet light-emitting diode 23a is used, and thus, the lighting apparatus may provide the sterilizing function without causing eye diseases or skin diseases.

Figure 11:
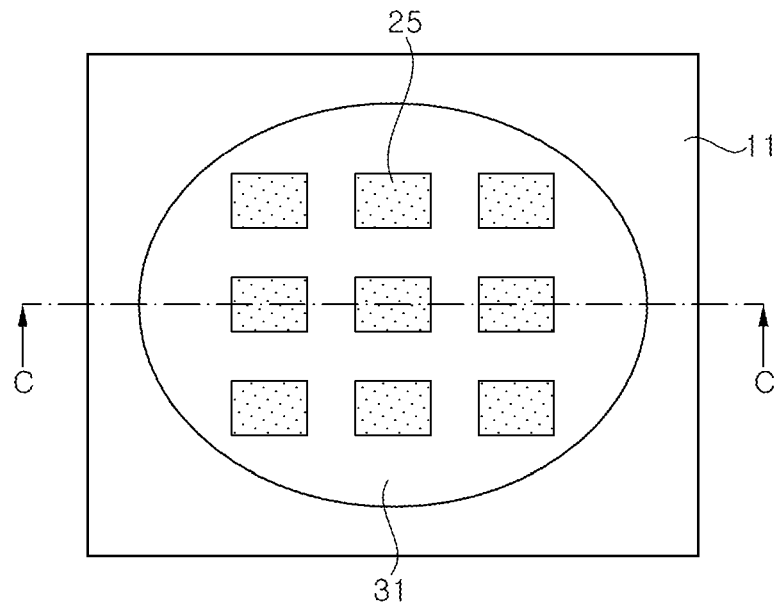
FIG. 11 is a schematic plan view of a lighting apparatus according to another exemplary embodiment.
Figure 12:
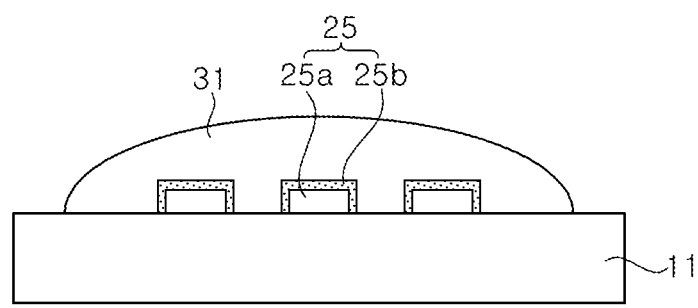
FIG. 12 is a schematic cross-sectional view taken along line C-C of FIG. 11.

FIG. 11 is a schematic plan view of a lighting apparatus according to another exemplary embodiment, and FIG. 12 is a schematic cross-sectional view taken along line C-C of FIG. 11.

Referring to FIG. 11 and FIG. 12, the lighting apparatus according to the illustrated exemplary embodiment is generally similar to that described above with reference to FIG. 1 and FIG. 2, except that each of light emitting units 25 includes a light emitting diode 25a and a wavelength converter 25b, which may further include a wavelength conversion substance in the near infrared region together with a wavelength conversion substance in the visible light region.

The light emitting diode 25a may be the light emitting diode 21a emitting UVB described with reference to FIG. 1 and FIG. 2, the violet light emitting diode 23a described with reference to FIG. 8 and FIG. 9, or a light emitting diode emitting other ultraviolet or blue light.

Light emitted from the light emitting diode 25a is absorbed by the wavelength conversion substance of the wavelength converter 25b and wavelength-converted, and the wavelength-converted light is emitted to the outside of the lighting apparatus. Furthermore, some of light generated by the light emitting diodes 25a may be emitted to the outside, and thus, the vitamin D producing function described with reference to FIG. 1 and FIG. 2 and the sterilizing function described with reference to FIG. 8 and FIG. 9 may be exhibited.

Meanwhile, the wavelength converter 25b includes a wavelength conversion substance that absorbs light generated by the light emitting diode 25a, and emits light having a longer wavelength than that of the absorbed light. The wavelength converter 25b may include, for example, a blue phosphor, a green phosphor, and a red phosphor as described above, or it may include a blue phosphor and an orange phosphor. In addition, when the light emitting diode 25a is a blue light emitting diode, the wavelength converter 25b may include a green phosphor and a red phosphor, or an orange phosphor. Types of these phosphors are substantially similar to those described with reference to FIG. 1 and FIG. 2, and thus, detailed descriptions thereof will be omitted to avoid redundancy.

The wavelength converter 25b includes a wavelength conversion substance emitting red light or near infrared light in a range of about 605 nm to about 935 nm. In particular, the wavelength conversion substance may emit light having a central wavelength in a range of, for example, 605 nm to 655 nm, 685 nm to 705 nm, 790 nm to 840 nm, or 875 nm to 935 nm.

Light having a wavelength in these ranges produces a cell activating substance in the mitochondria. More particularly, the cytochrome c oxidase in the mitochondria absorbs light in the range of 605 nm to 935 nm as a photoreceptor to increase its activity, and thereby produces nitric oxide (NO). NO improves human health by affecting pain relief and improving blood circulation. In addition, the activity of the cytochrome c oxidase protein contributes to ATP production, and also affects cell damage treatment.

Figure 13:
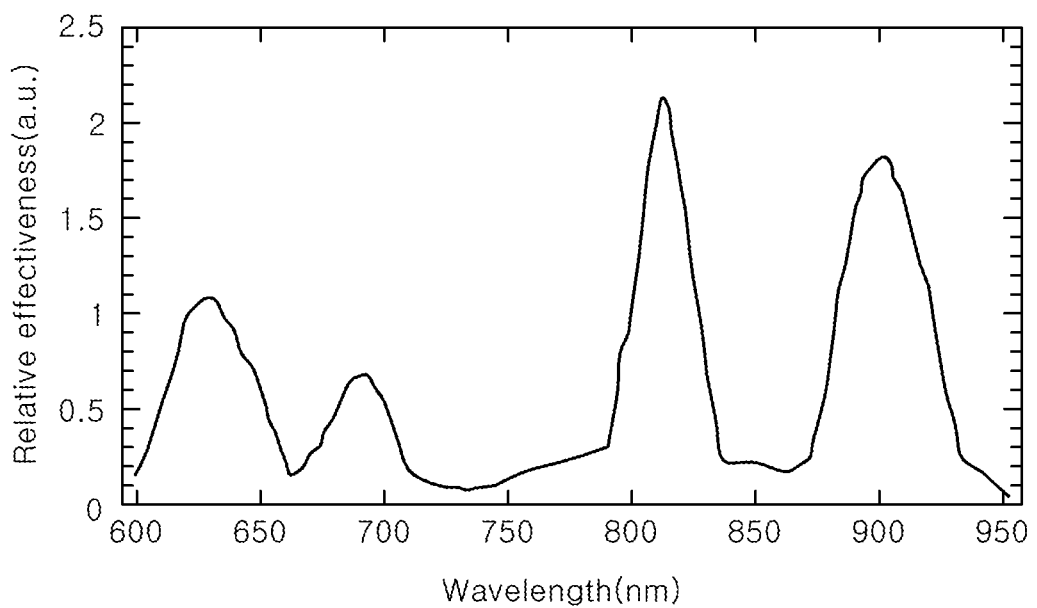
FIG. 13 is a graph showing effectiveness of cell function activity according to wavelengths.

In particular, an energy absorption rate of cytochrome c oxidase is relatively high in the range of 605 nm to 655 nm, 685 nm to 705 nm, 790 nm to 840 nm, or 875 nm to 935 nm. More particularly, the energy absorption rate of cytochrome c oxidase, as shown in FIG. 13, exhibits the highest absorption in the range of 790 nm to 840 nm, followed by in the range of 875 nm to 935 nm, and then in the range of 605 nm to 655 nm.

Since the wavelength conversion substance according to the illustrated exemplary embodiment emits light having a wavelength that promotes the relatively high energy absorption in the cytochrome c oxidase, efficiency of health promotion may be improved.

The wavelength conversion substance may be a phosphor or a quantum dot. In particular, the quantum dot may have a narrow half width, and thus, it may be more suitable for producing the cell activating substance.

Since the wavelength conversion substance emitting light in the range of 605 nm to 655 nm overlaps with the wavelength conversion substance for implementing white light, it does not need to be added separately. In order not to affect the color temperature of the white light emitting device, a wavelength conversion substance emitting light in a low visibility range, in particular, light having the central wavelength in the range of about 685 to 705 nm, 790 to 840 nm, or 875 to 935 nm may be mainly used.

Meanwhile, for cell activation, irradiance of light emitted from the lighting apparatus may be 570 $W/m^2$ or less, and further, may be 100 $W/m^2$ or less. 570 $W/m^2$ represents a limit value of risk group 1 for light in the infrared range in the Photobiological Safety Standard (IEC 62471), and 100 $W/m^2$ corresponds to an exempt. The lighting apparatus according to an exemplary embodiment has the radiance of 570 $W/m^2$ or less, and thus, the lighting apparatus may be driven to produce a cell activating substance without harming the human body for a relatively long period of time.

According to the exemplary embodiments, the lighting apparatus may be used to promote the health of the human body not only in the indoor living space but also in a space where a large number of people are active, such as an airport or a hospital.

According to the exemplary embodiments, the lighting apparatus is capable of emitting light that generates the cell activating substance along with white light while using a single type of light emitting diode 25a. Furthermore, depending on a type of the light emitting diode 25a, the lighting apparatus may additionally provide vitamin D synthesis or sterilizing function.

Figure 14:
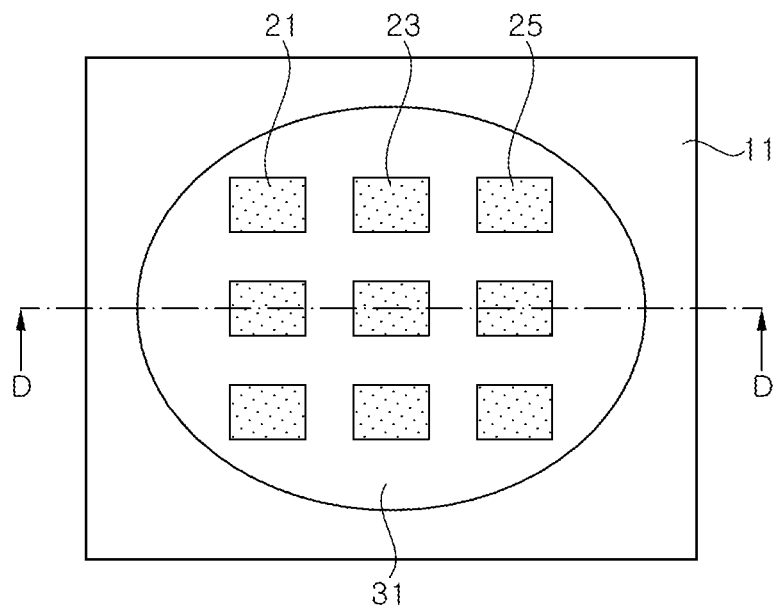
FIG. 14 is a schematic plan view of a lighting apparatus according to another exemplary embodiment.
Figure 15:
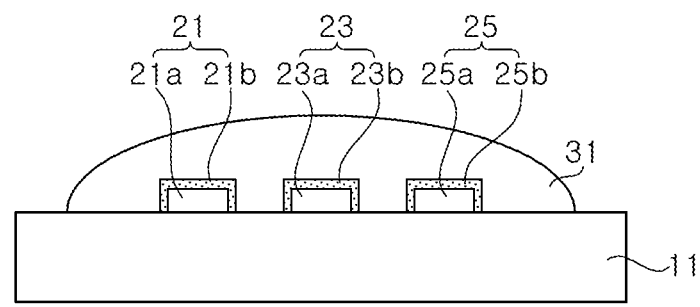
FIG. 15 is a schematic cross-sectional view taken along line D-D of FIG. 14.

FIG. 14 is a schematic plan view of a lighting apparatus according to another exemplary embodiment, and FIG. 15 is a schematic cross-sectional view taken along line D-D of FIG. 14.

Referring to FIG. 14 and FIG. 15, the lighting apparatus according to the illustrated exemplary embodiment is generally similar to that described with reference to FIG. 1 and FIG. 2, except that light emitting units 21, 23, and 25 include different light emitting diodes 21a, 23a, and 25a from each other.

The light emitting unit 21 is substantially the same as the light emitting unit 21 described with reference to FIG. 1 and FIG. 2, the light emitting unit 23 is substantially the same as that described with reference to FIG. 8 and FIG. 9, and the light emitting unit 25 is substantially the same as the light emitting unit 25 described with reference to FIG. 11 and FIG. 12.

The light emitting units 21, 23, and 25 may be disposed on the circuit board 11 in various ways. For example, the light emitting units 21, 23, and 25 may be disposed so that light emitting units of the same kind are disposed in the same row, or light emitting units of the same kind may be disposed to be far from each other.

In addition, the light emitting units 21, 23, and 25 may be electrically connected to one another to independently drive the same kind of light emitting units, and thus, a certain function may be performed simultaneously or at different times.

For example, when each of the light emitting units 21, 23, and 25 is operated, vitamin D production, sterilization, and cell activating functions may be performed together. In addition, when the light emitting units 21, 23, and 25 are individually operated, any one or more of vitamin D production, sterilization, and cell activation functions may be performed.

According to the illustrated exemplary embodiment, the lighting apparatus may be programmed to adjust a time zone in which vitamin D production is active, a time zone in which sterilizing function is active, and a time zone in which cell activating function is active. For example, vitamin D production may be performed primarily at a time zone near noon.

Although the lighting apparatus is illustrated as including all three kinds of light emitting units 21, 23, and 25, however, the inventive concepts are not limited thereto. For example, in some exemplary embodiments, the lighting apparatus may include any two light emitting units among the three kinds of light emitting units 21, 23, and 25.

In some exemplary embodiments, the light emitting units 23 and 25 may be provided in a package form like the light emitting unit 21 described with reference to FIG. 7. Furthermore, in some exemplary embodiments, a diffusion plate may be added to uniformly mix light emitted from the light emitting units 21, 23, and 25.

Figure 16:
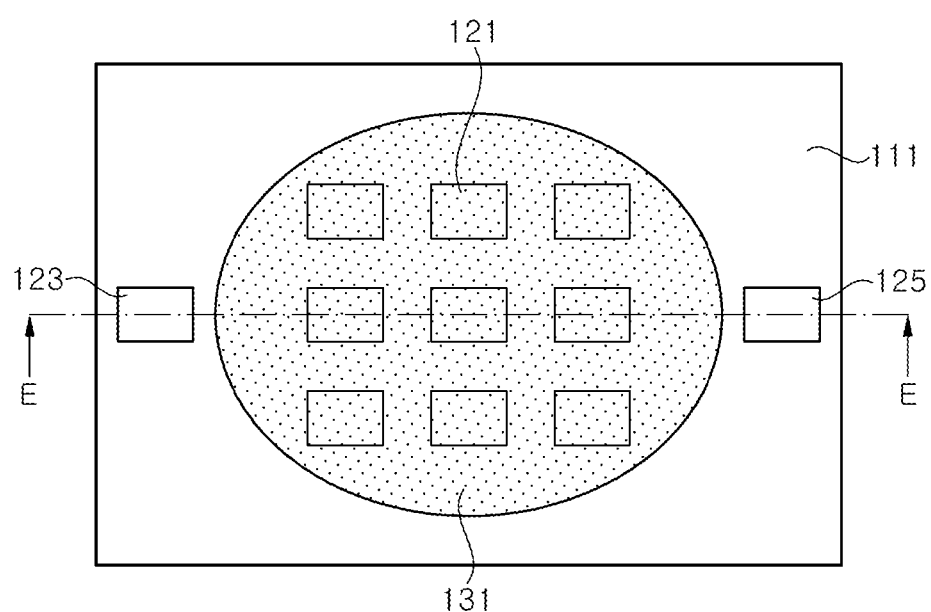
FIG. 16 is a schematic plan view of a lighting apparatus according to an exemplary embodiment.
Figure 17:
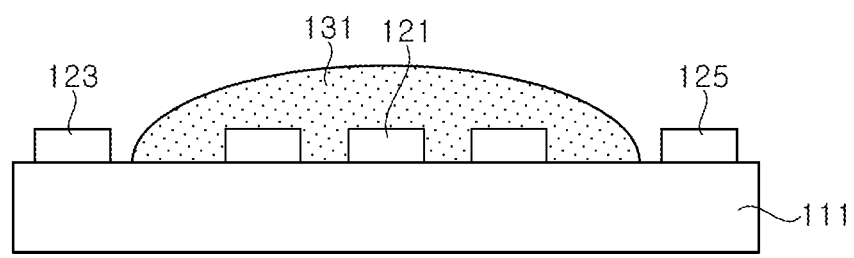
FIG. 17 is a schematic cross-sectional view taken along line E-E of FIG. 16.

FIG. 16 is a schematic plan view of a lighting apparatus according to an exemplary embodiment, and FIG. 17 is a schematic cross-sectional view taken along line A-A of FIG. 16.

Referring to FIG. 16 and FIG. 17, the lighting apparatus may include a circuit board 111, a first light emitting diode 121, a second light emitting diode 123, a third light emitting diode 125, and a wavelength converter 131.

The circuit board 111 may have a circuit pattern for supplying power to the first to third light emitting diodes 121, 123, and 125. The circuit board 111 may be a printed circuit board, for example, a metal-PCB. The circuit board 111, on which the first to third light emitting diodes 121, 123, and 125 are mounted, may be disposed in the lighting apparatus as a light emitting module.

At least one first light emitting diode 121 may be mounted on the circuit board 111 as a light source to implement white light. The first light emitting diode 121 may be an inorganic light emitting diode, which may be formed by a group III nitride semiconductor, such as an AlGaInN-based semiconductor. The first light emitting diode 121 may have a flip chip type, a vertical type, or a horizontal type structure, without being limited thereto.

A plurality of first light emitting diodes 121 may be electrically connected to one another in various ways, for example, in series, in parallel, or in series/parallel. The plurality of first light emitting diodes 121 may be disposed in various ways according to the lighting apparatus. For example, the plurality of first light emitting diodes 121 may be disposed in two dimensions for a surface lighting apparatus, and the first light emitting diodes 121 may be disposed along a line for a tubular lighting apparatus.

The first light emitting diode 121 according to the illustrated exemplary embodiment may emit ultraviolet light or visible light, and may have a peak wavelength in a range of about 300 nm to about 470 nm. In particular, the first light emitting diode 121 may have a peak wavelength in a range of about 400 nm to about 420 nm. When the first light emitting diode 121 emits ultraviolet light, most of the ultraviolet light is wavelength-converted by the wavelength converter 131, thereby preventing the ultraviolet light from being emitted from the first light emitting diode 121 to the outside. Furthermore, when the first light emitting diode emits light having the peak wavelength in the range of 400 nm to 420 nm, the safety problem associated with ultraviolet light may be eliminated in advance. Furthermore, an energy loss from the wavelength conversion may be reduced as compared to when the ultraviolet light is emitted, thereby preventing potential eye diseases or skin diseases caused by blue light, which will be described in more detail later.

The wavelength converter 131 converts a wavelength of light emitted from the first light emitting diode 121. The wavelength converter 131 may be, for example, a molding member including a phosphor or a quantum dot. The wavelength converter 131 covers the first light emitting diode 121. When the plurality of first light emitting diodes 121 are mounted on the circuit board 111, the wavelength converter 131 may cover each of the plurality of first light emitting diodes 121.

The wavelength converter 131 includes a wavelength converting substance for implementing white light together with light emitted from the first light emitting diode 121. In an exemplary embodiment, the wavelength converter 131 may include a blue phosphor, a green phosphor, and a red phosphor. In another exemplary embodiment, the wavelength converter 131 may include a blue phosphor and an orange phosphor. In some exemplary embodiments, when the first light emitting diode 121 is a blue light emitting diode, the wavelength converter 131 may include a green phosphor and a red phosphor, or an orange phosphor, without a blue phosphor. In another exemplary embodiment, the wavelength converter may include quantum dots instead of, or in addition to the phosphor.

The blue phosphor may be a BAM-based, a halo-phosphate-based, or an aluminate-based phosphor, and may include, for example, $BaMgAl_{10}O_{17}:Mn^{2+}$, $BaMgAl_{12}O_{19}:Mn^{2+}$ or $(Sr,Ca,Ba)PO_4Cl:Eu^{2+}$. The blue phosphor may have, for example, a peak wavelength in a range of 440 nm to 500 nm.

The green phosphor may include $LuAG(Lu_3(Al,Gd)_5O_{12}:Ce^{3+})$, $YAG(Y_3(Al,Gd)_5O_{12}:Ce^{3+})$, $Ga—LuAG((Lu,Ga)_3(Al,Gd)_5O_{12}:Ce^{3+})$, $Ga-YAG$ $((Ga,Y)_3(Al,Gd)_5O_{12}:Ce^{3+})$, $LuYAG$ $((Lu,Y)_3(Al,Gd)_5O_{12}:Ce^{3+})$, ortho-silicate $((Sr,Ba,Ca,Mg)_2SiO_4:Eu^{2+})$, oxynitride $((Ba,Sr,Ca)Si_2O_2N_2:Eu^{2+})$, $β$-$SiAlON:Eu^{2+}$, $Ca$-$α$-$SiAlON:Eu^{2-}$, or thio gallate $(SrGa_2S_4:Eu^{2+})$. The green phosphor may have a peak wavelength in a range of 500 nm to 600 nm.

The red phosphor may be a nitride-based, a sulfide-based, a fluoride or an oxynitride-based phosphor, and, may include CASN(CaAlSiN$_3$:Eu$^{2+}$), (Ba,Sr,Ca)$_2$Si$_5$N$_8$:Eu$^{2+}$, (Ca,Sr)S$_2$:Eu$^{2+}$, or (Sr,Ca)$_2$SiS$_4$:Eu$^{2+}$. The red phosphor may have a peak wavelength in a range of 600 nm to 700 nm.

White light having various color temperatures may be implemented by a combination of the first light emitting diode 121 and the wavelength converter 131.

As described above, blue light is generally known to cause the eye diseases and skin diseases.

Figure 18:
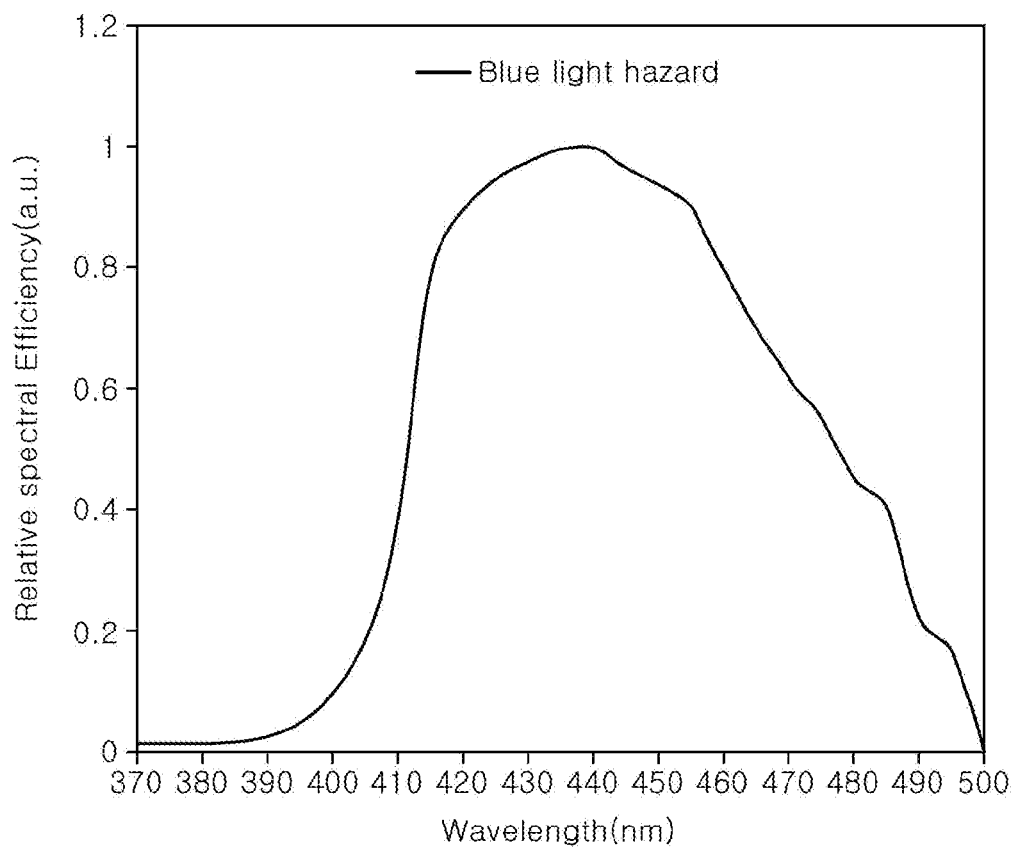
FIG. 18 is a graph showing a degree of hazard according to wavelengths of blue light.

FIG. 18 is a graph showing a degree of hazard according to wavelengths of blue light.

Referring to FIG. 18, the highest degree of hazard is exhibited in a wavelength range between about 430 nm and about 440 nm. A wavelength range of 420 nm to 455 nm exhibits 90% or more degree of hazard based on the highest hazard value, a wavelength range of 413 nm to 465 nm exhibits 70% or more degree of hazard, and a wavelength range of 411 nm to 476 nm exhibits 50% or more degree of hazard. Ultraviolet light is known to harm the human body and, in particular, exhibits the highest degree of hazard between 270 nm and 280 nm.

Figure 19:
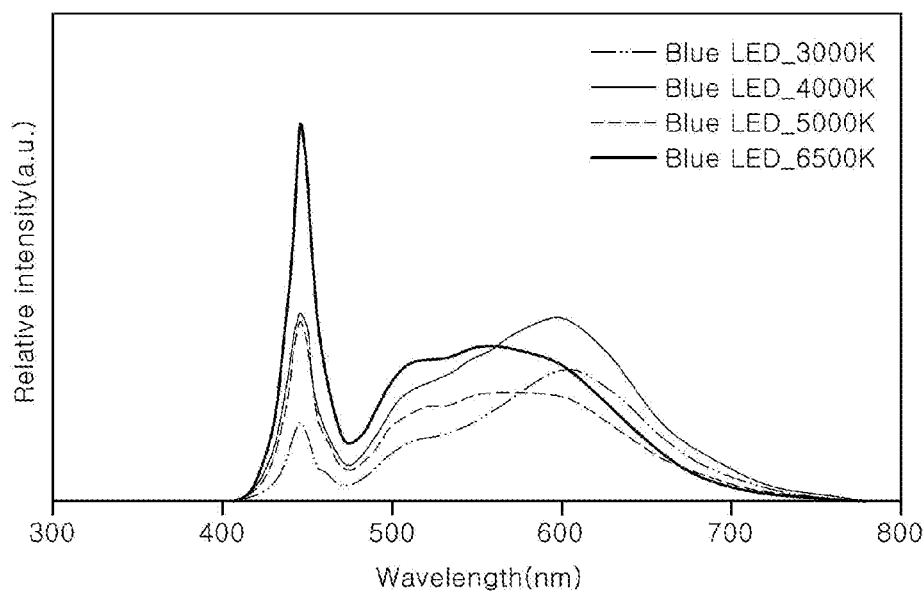
FIG. 19 is a graph showing a spectrum of a white light source using a blue light emitting diode.

FIG. 19 shows a spectrum of a conventional white light source using a general blue light emitting diode 121.

Referring to FIG. 19, a conventional white light source may implement white light using a yellow phosphor, or a green phosphor and a red phosphor together with the blue light emitting diode. A type and an amount of phosphor are controlled according to a desired color temperature, and an intensity of the blue light may be increased as the color temperature increases.

The blue light emitting diode used in the conventional white light source generally has a peak wavelength in a range of about 430 nm to about 470 nm. Blue light in this range has a relatively high degree of hazard as shown in FIG. 18. As such, as the desired color temperature of the white light source increases, the intensity of the blue light may be increased, thereby increasing the hazard of causing eye diseases or skin diseases.

Figure 20:
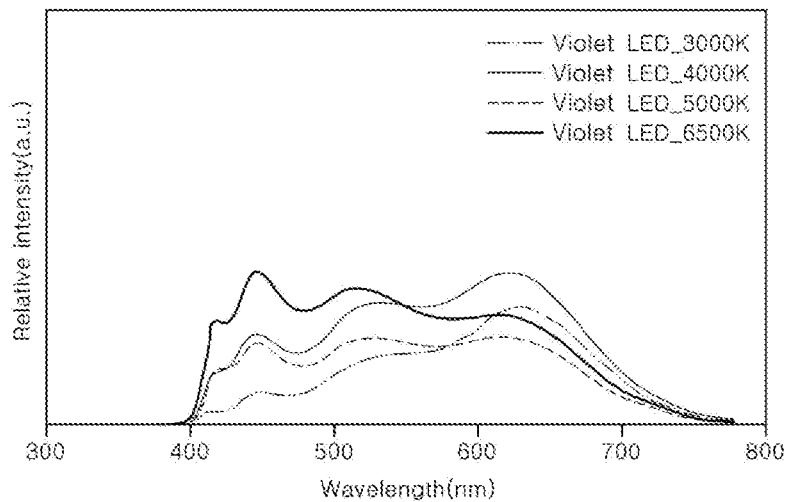
FIG. 20 is a graph showing spectra of white light sources according to exemplary embodiments.

FIG. 20 is a graph showing spectra of white light sources according to exemplary embodiments. In particular, FIG. 20 shows exemplary spectra of white light having various color temperatures implemented by a combination of a violet light emitting diode 121 and a wavelength converter 131.

Referring to FIG. 20, white light of each color temperature is implemented by a combination of light emitted from phosphors and light emitted from the violet light emitting diode 121 having a peak wavelength in a range of about 400 nm to about 420 nm.

As described above, the wavelength converter 131 includes a blue phosphor, and may further include a green phosphor and a red phosphor. These phosphors may absorb light emitted from the violet light emitting diode 121 and emit blue light, green light, and red light.

White light of various color temperatures shown in FIG. 20 may have a peak due to the violet light emitting diode 121 and a peak due to the blue phosphor. These peaks may be more distinct as the color temperature rises. The peak due to the violet light emitting diode 121 and the peak due to the blue phosphor are located at different wavelengths from each other. In particular, since the blue phosphor converts a wavelength of light emitted from the violet light emitting diode 121 into a longer wavelength, the peak by the blue phosphor is located at a longer wavelength than that of the peak by the violet light emitting diode 121.

In addition, irradiance of light emitted from the light emitting diode 121 at each color temperature may be less than that of light emitted from the blue phosphor. As the color temperature increases, although the irradiance of light emitted from the light emitting diode 121 may be increased, irradiance of blue light emitted from the blue phosphor may be increased at a greater extent. In addition, the irradiance of light emitted from the light emitting diode 121 may be less than that of light emitted from the green phosphor, and may be less than that of light emitted from the red phosphor.

Accordingly, the lighting apparatus according to the illustrated exemplary embodiment may further prevent the occurrence of eye diseases or skin diseases caused by light emitted from the first light emitting diode 121. However, as described above, since the wavelength in about 400 nm to about 420 nm range has a relatively low hazard to the human body, the irradiance thereof may be further increased.

Further, light emitted from the light emitting diode 121 having the peak wavelength in the range of about 400 nm to about 420 nm may have a sterilizing function. For example, the light emitting diode 121 may emit light having a peak wavelength of about 400 nm to about 410 nm, and more particularly, a peak wavelength of about 405 nm. Short wavelength visible light in the range of about 400 nm to about 420 nm has a relatively low hazard to eye diseases or skin diseases, and has a high sterilizing capacity against pathogenic microorganisms. As such, the short wavelength visible light may be suitably used for the lighting apparatus to perform the sterilizing function.

Referring back to FIG. 16 and FIG. 17, the second light emitting diode 123 may emit ultraviolet light of UVB, and may emit light having a peak wavelength in a range of about 286 nm to about 304 nm, more specifically, in a range of about 291 nm to about 301 nm. When ultraviolet light in this range is irradiated to the human body, vitamin D may be efficiently synthesized. The second light emitting diode 123 may be an inorganic light emitting diode, which may be formed by a group III nitride semiconductor, without being limited thereto. The second light emitting diode 123 may have a flip chip type, a vertical type, or a horizontal type structure, without being limited thereto.

The second light emitting diode 123 may be mounted on the circuit board 111 while being spaced apart from the wavelength converter 131. In this manner, light emitted from the second light emitting diode 123 may be prevented from being absorbed by the wavelength converter 131. Accordingly, irradiance of light emitted from the second light emitting diode 123 may be improved. In addition, the second light emitting diode 123 is spaced apart from the wavelength converter 131, and thus, light emitted from the second light emitting diode 123 may be prevented from wavelength conversion, thereby preventing energy loss due to the stoke shift. However, the inventive concepts are not limited thereto, and in some exemplary embodiments, the second light emitting diode 123 may be disposed in the wavelength converter 131.

Ultraviolet light generated in the second light emitting diode 123 and emitted to the outside may be used for the synthesis of vitamin D. It is known that 7-dehydrocholesterol in skin cells reacts with UVB to synthesize cholecalciferol (vitamin D3).

Figure 21:
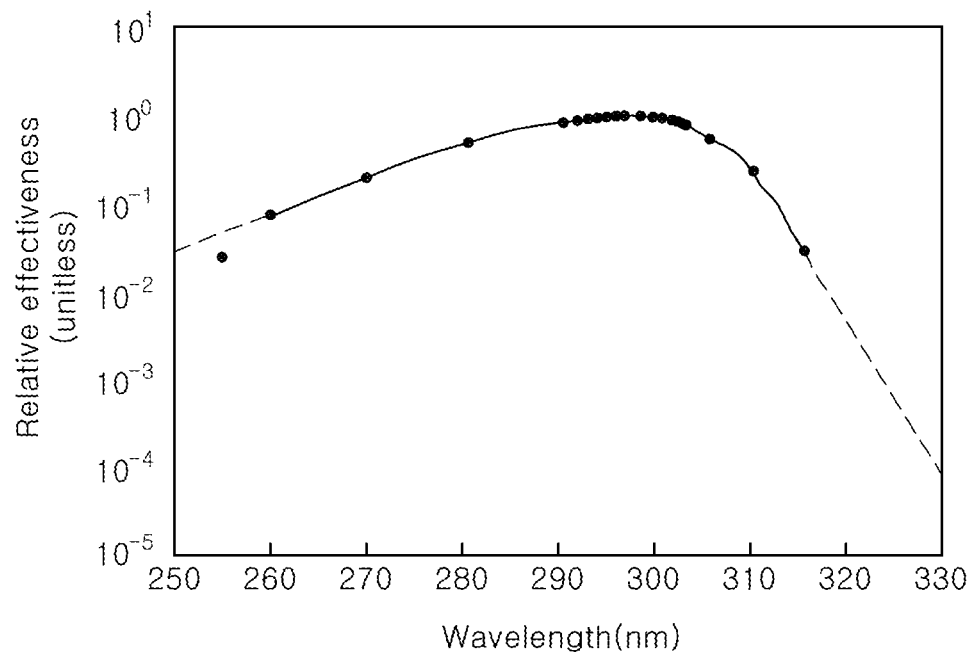
FIG. 21 is a graph showing effectiveness of vitamin D production in the human body according to wavelengths.

FIG. 21 is a graph showing effectiveness of vitamin D production in the human body according to wavelengths, which was published in CIE 174: 2006.

Referring to FIG. 21, ultraviolet light of about 298 nm is most efficient for vitamin D production, and that in a range of about 291 nm to about 301 nm exhibits an efficiency of about 90% or more of the highest efficiency. In addition, ultraviolet light in a range of about 286 nm to about 304 nm exhibits about 70% or more efficiency of the highest efficiency, and that in a range of about 281 nm to about 306 nm exhibits about 50% or more efficiency of the highest efficiency. When a peak wavelength of the light emitting diode 123 is about 298 nm, it is the most efficient for vitamin D production, and, within the range of about 286 nm to about 304 nm, it will exhibit a relatively favorable efficiency of 70% or more for vitamin D production.

As described above, vitamin D is involved in calcium metabolism, and a deficiency of vitamin D may cause a major impediment to bone growth. A recommended daily dose of vitamin D, which is generally suggested to maintain an adequate level of vitamin D, varies from country to country, generally in a range of about 400 IU to about 800 IU, and has been adjusted upward. For example, the International Commission on Illumination (CIE) suggests the required UVB exposure to produce 1000 IU of vitamin D, which is about 21 $J/m^2$ to about 34 $J/m^2$ for the entire body of the second skin type based on the sunlight at noon in midsummer. Meanwhile, a reference dose for the human exposure safety range for UVB provided by the American Conference of Governmental Industrial Hygienists (ACGIH) is 47 $J/m^2$ for 290 nm, about 65 $J/m^2$ for 297 nm, and 100 $J/m^2$ for 300 nm.

As such, a dose of UVB irradiated by the lighting apparatus may need to be adjusted, such that the UVB dosage may be used for vitamin D synthesis while not exceeding the safety range. In addition, since the daily permissible reference dose increases as the wavelength increases in the ultraviolet region of UVB, the second light emitting diode 123 having a peak wavelength of 298 nm or longer, for example, about 298 nm to about 301 nm, may emit a greater amount of ultraviolet light, thereby making the lighting apparatus more suitable for the vitamin D synthesis function.

The second light emitting diode 123 may be driven independently from the first light emitting diode 121, and thus, may be turned on or off as needed while the first light emitting diode 121 is operating.

The third light emitting diode 125 may be mounted on the circuit board 111 while being apart from the wavelength converter 131. Light emitted from the third light emitting diode 125 may be emitted to the outside without actually entering the wavelength converter 131. Accordingly, irradiance of light emitted from the third light emitting diode 125 may be improved.

The third light emitting diode 125 may be connected to the first light emitting diode 121 in series or in parallel, or may be driven independently from the first light emitting diode 121.

The third light emitting diode 125 emits light suitable for cell activation. The third light emitting diode 125 may emit light having a peak wavelength in a range of about 605 nm to about 935 nm, without being limited thereto. The third light emitting diode may be formed of, for example, an AlGaInP-based or AlGaInAs-based semiconductor.

Red light or near infrared light in the range of about 605 nm to about 935 nm produces a cell activating substance in the mitochondria. More particularly, the cytochrome c oxidase in the mitochondria absorbs light in the range of 605 nm to 935 nm as a photoreceptor to increase its activity, and thereby, produces nitric oxide (NO). NO improves human health by affecting pain relief and improving blood circulation. In addition, the activity of the cytochrome c oxidase protein contributes to ATP production, and also affects cell damage treatment.

Figure 22:
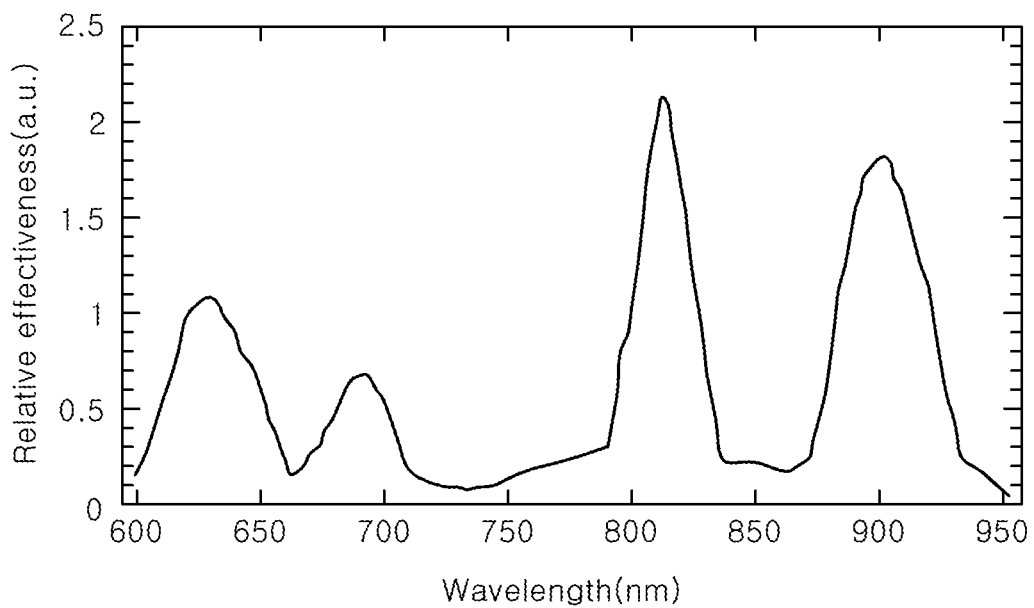
FIG. 22 is a graph showing effectiveness of cell function activity according to wavelengths.

In particular, the third light emitting diode 125 may emit light having a peak wavelength in a range of about 605 nm to about 655 nm, about 685 nm to about 705 nm, about 790 nm to about 840 nm, or about 875 nm to about 935 nm. In this range, the energy absorption rate of cytochrome c oxidase is relatively high. More particularly, as shown in FIG. 22, the energy absorption rate of cytochrome c oxidase exhibits the highest absorption in the range of 790 nm to 840 nm, followed by in the range of about 875 nm to about 935 nm, and then in the range of about 605 nm to about 655 nm.

Since the third light emitting diode 125 emits light having a wavelength that promotes the relatively high energy absorption in cytochrome c oxidase, efficiency of health promotion may be improved.

Further, when a plurality of third light emitting diodes 125 are used, light emitting diodes emitting light in a specific wavelength range as described above, such as in the range of 790 nm to 840 nm, or 875 nm to 935 nm having the high efficiency may be used plural. As such, various light emitting diodes may be used to evenly emit light in each wavelength range.

In addition, since the light emitting diode emitting light in the range of 605 nm to 655 nm may affect the color temperature of white light, the third light emitting diodes 125 may be formed to emit light having a peak wavelength in a low visibility range, such as in a range of about 685 nm to about 705 nm, about 790 nm to about 840 nm, or about 875 nm to about 935 nm, in order to minimize affecting the color temperature of the white light emitting device.

According to an exemplary embodiment, to add a cell activating function to the lighting apparatus, irradiance of light emitted from the third light emitting diode 125 may be greater than those from the first light emitting diodes 121 and the wavelength converter 131 that implement white light at the same wavelength. Accordingly, the cell activating function may be performed by the third light emitting diode 125.

According to an exemplary embodiment, a driving time of the third light emitting diode 125 and that of the first light emitting diode 121 may be substantially the same, however, the inventive concepts are not limited thereto. For example, the driving time of the third light emitting diode 125 may be adjusted according to an installation location of the lighting apparatus. In particular, the use time or the amount of irradiance of the third light emitting diode 125 may be adjusted in consideration of the risk to the human body.

For example, the irradiance of light emitted from the third light emitting diode 125 of the lighting apparatus may be 570 $W/m^2$ or less, and further, may be 100 $W/m^2$ or less. 570 $W/m^2$ represents a limit value of risk group 1 for light in the infrared range in the Photobiological Safety Standard (IEC 62471), and 100 $W/m^2$ corresponds to an exempt. The lighting apparatus according to an exemplary embodiment has the radiance of 570 $W/m^2$ or less, and thus, the lighting apparatus may be driven to produce a cell activating substance without harming the human body for a relatively long period of time.

According to an exemplary embodiment, the lighting apparatus may include more first light emitting diodes 121 than the third light emitting diodes 125, and thus, may emit light having an intensity suitable for illumination. However, the inventive concepts are not limited thereto.

The third light emitting diode 125 according to the illustrated exemplary embodiment is described as emitting light for performing the cell activating function, but in some exemplary embodiments, a wavelength converting substance may be used instead of the third light emitting diode 125. For example, a phosphor or a quantum dot emitting light in the red region or the infrared region may be used. In particular, since the quantum dot has a narrow half-width, the quantum dot may emit light having a wavelength suitable for the cell activating function. The wavelength converting substance having the cell activating function may be included in the wavelength converter 131 to convert light generated by the first light emitting diode 121, and may be disposed on a light emitting diode different from the first light emitting diode 121. In this case, the different light emitting diode may emit light having a longer wavelength than that of the first light emitting diode 121, and thus, energy loss due to wavelength conversion may be reduced.

The lighting apparatus according to the illustrated exemplary embodiment may be used to promote the health of the human body not only in the indoor living space, but also in a space where a large number of people are active, such as an airport or a hospital.

FIG. 16 and FIG. 17 exemplarily illustrate that the plurality of first light emitting diodes 121, a single second light emitting diode 123, and a single third light emitting diode 125 are disposed on the substrate 111, however, in some exemplary embodiments, at least one of the second light emitting diodes 123 and the third light emitting diodes 125 may be formed in plural on the substrate 111.

Figure 23:
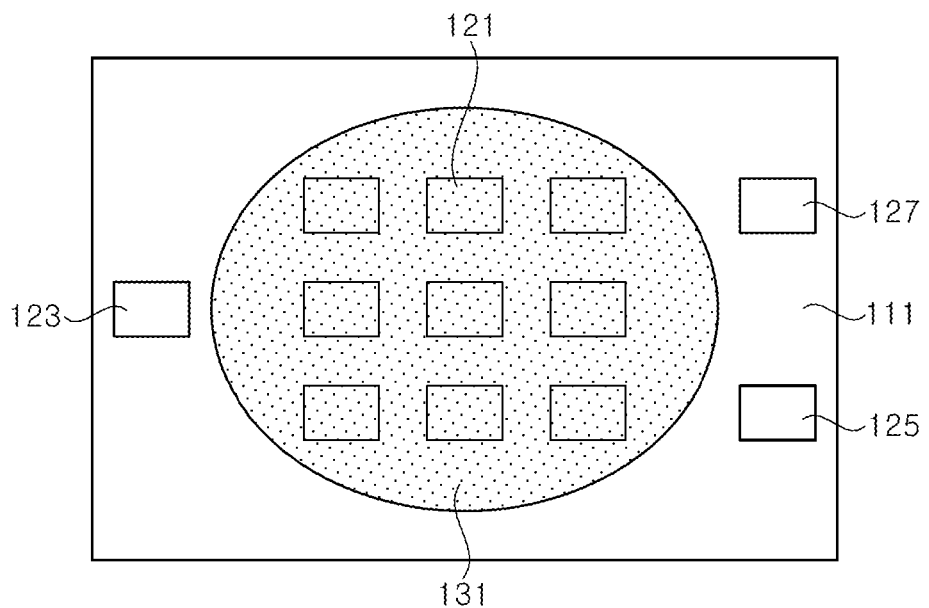
FIG. 23 is a schematic plan view of a lighting apparatus according to another exemplary embodiment.

FIG. 23 is a schematic plan view of a lighting apparatus according to another exemplary embodiment.

Referring to FIG. 23, the lighting apparatus according to the illustrated exemplary embodiment is generally similar to that described with reference to FIG. 16 and FIG. 17, except a fourth light emitting diode 127. As such, repeated descriptions of substantially the same elements of the lighting apparatus will be omitted, and the fourth light emitting diode 127 will be described in more detail.

The fourth light emitting diode 127 may be mounted on the circuit board 111 while being spaced apart from the wavelength converter 131. Light emitted from the fourth light emitting diode 127 may be emitted to the outside without actually entering the wavelength converter 131. Accordingly, irradiance of light emitted from the fourth light emitting diode 127 may be improved.

The fourth light emitting diode 127 may be connected to the first light emitting diode 121 in series or in parallel, or may be driven independently from the first light emitting diode 121.

The fourth light emitting diode 127 may emit light other than white light and suitable for sterilizing pathogenic microorganisms. The fourth light emitting diode 127 may emit light having a peak wavelength of about 400 nm to about 420 nm, a peak wavelength of about 400 nm to about 410 nm, or a peak wavelength of about 405 nm depending upon applications. The wavelength of about 405 nm may be absorbed by porphyrin, a substance existing in the cells of bacteria, to generate reactive oxygens, and the generated reactive oxygens may be accumulated and destroy cell walls. As such, the wavelength in the visible range of the above range is suitable for sterilizing pathogenic microorganisms without causing eye diseases or skin diseases.

The fourth light emitting diode 127 may emit light having the same wavelength as that of the first light emitting diode 121, however, the inventive concepts are not limited thereto. For example, in some exemplary embodiments, the fourth light emitting diode 127 may emit light having a wavelength different from that of the first light emitting diode 121. The fourth light emitting diode 127 is disposed separately from the first light emitting diode 121, and thus, the sterilizing function may be efficiently provided.

According to the illustrated exemplary embodiment, to add the cell activating function to the lighting apparatus, irradiance of light emitted from the fourth light emitting diode 127 may be greater than that of the white light source at the same wavelength. Furthermore, irradiance of light emitted from the fourth light emitting diode 127 may be greater than that of light emitted from the first light emitting diode 121 to the outside of the lighting apparatus. In this manner, the sterilizing function is mainly performed by the fourth light emitting diode 127 as compared with the first light emitting diode 121.

According to an exemplary embodiment, a driving time of the fourth light emitting diode 127 and that of the first light emitting diode 121 may be substantially the same, however, the inventive concepts are not limited thereto. In some exemplary embodiments, the driving time of the fourth light emitting diode 127 may be adjusted according to an installation location of the lighting apparatus. In particular, the use time or the amount of irradiance of the fourth light emitting diode 127 may be adjusted in consideration of the risk to the human body.

For example, irradiance of the fourth light emitting diode 127 emitted from the lighting apparatus may be 1 $W/m^2$ or less, and further, may be 0.1 $W/m^2$ or less. 1 $W/m^2$ represents a limit value of risk group 1 for blue light in a range 300 nm to 700 nm in the Photobiological Safety Standard (IEC 62471), and 0.1 $W/m^2$ corresponds to an exempt. The lighting apparatus according to an exemplary embodiment has the radiance of 1 $W/m^2$ or less, and thus, the lighting apparatus may be driven to sterilize for a relatively long period of time in the lighting apparatus.

According to an exemplary embodiment, pathogenic microorganisms may be sterilized not only in the indoor living space, but also in a space where a large number of people work, such as an airport or a hospital, thereby preventing human infection by pathogenic microorganisms.

Figure 24:
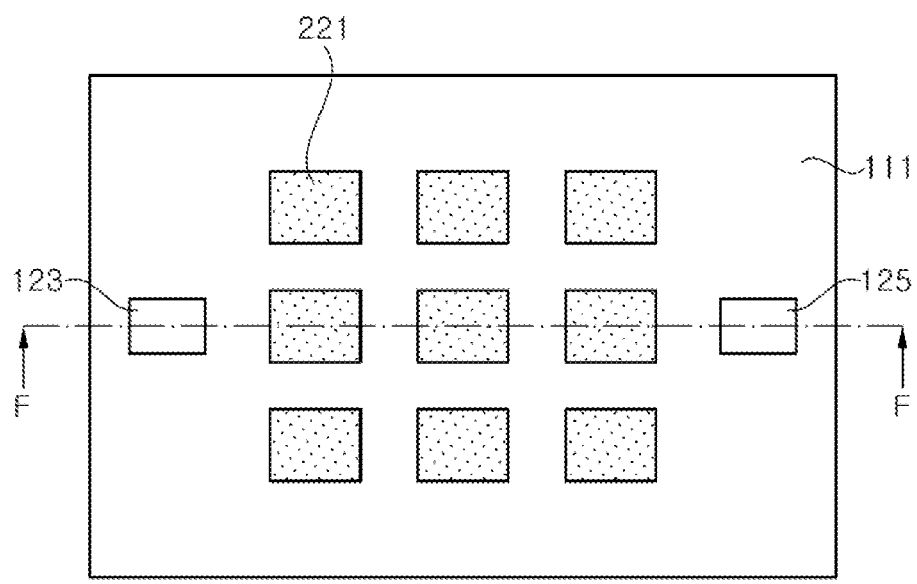
FIG. 24 is a schematic plan view of a lighting apparatus according to another exemplary embodiment.
Figure 25:
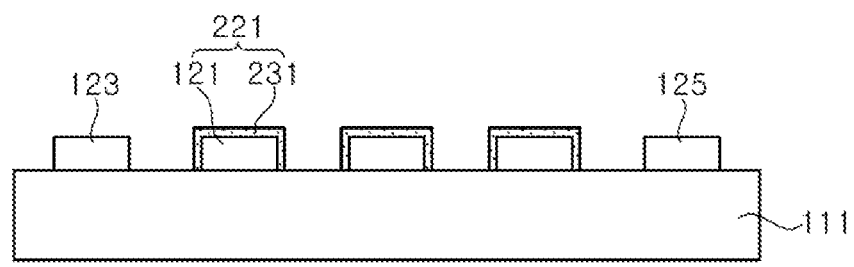
FIG. 25 is a schematic cross-sectional view taken along line F-F of FIG. 24.

FIG. 24 is a schematic plan view of a lighting apparatus according to another exemplary embodiment, and FIG. 25 is a schematic cross-sectional view taken along line F-F of FIG. 24.

Referring to FIG. 24 and FIG. 25, the lighting apparatus according to the illustrated exemplary embodiment is generally similar to that described with reference to FIG. 16 and FIG. 17, except that wavelength converters 231 are formed on the first light emitting diodes 121, respectively. More particularly, the wavelength converter 131 of FIGS. 16 and 17 covers each of the plurality of first light emitting diodes 121, while in the illustrated exemplary embodiment, each first light emitting diode 121 is individually covered with the wavelength converter 231.

Wavelength converting substances in the first to third light emitting diodes 121, 123, and 125 and the wavelength converter 231 are substantially the same as those described above, and thus, repeated descriptions thereof will be omitted.

Since the first light emitting diodes 121 are covered with the wavelength converter 231, respectively, in some exemplary embodiments, the second light emitting diode 123 and the third light emitting diode 125 may be disposed between the first light emitting diodes 121. In addition, the plurality of second light emitting diodes 123 and the plurality of third light emitting diodes 125 may be uniformly distributed between the first light emitting diodes 121, and thus, light emitted from the second light emitting diodes 123 and the third light emitting diode 125 may be mixed with white light. In some exemplary embodiments, the second light emitting diode 123 or the third light emitting diode 125 may be covered with a transparent molding member for protection from an external environment.

In the illustrated exemplary embodiment, a light source unit 221 for lighting is provided by the first light emitting diode 121 and the wavelength converter 231. Each light source unit 221 may implement white light by a combination of the first light emitting diode 121 and the wavelength converter 231. According to an exemplary embodiment, the light source units 221 may implement white light having the same color temperature. In another exemplary embodiment, the light source units 221 may implement white light having different color temperatures. For example, the light emitting diodes 121 may emit light having different peak wavelengths, and the wavelength converters 231 may include different wavelength converting substances from each other. In some exemplary embodiments, the light source units 221 may implement light of a different color instead of white light, and white light may be implemented by a combination of these light source units 221.

Figure 26:
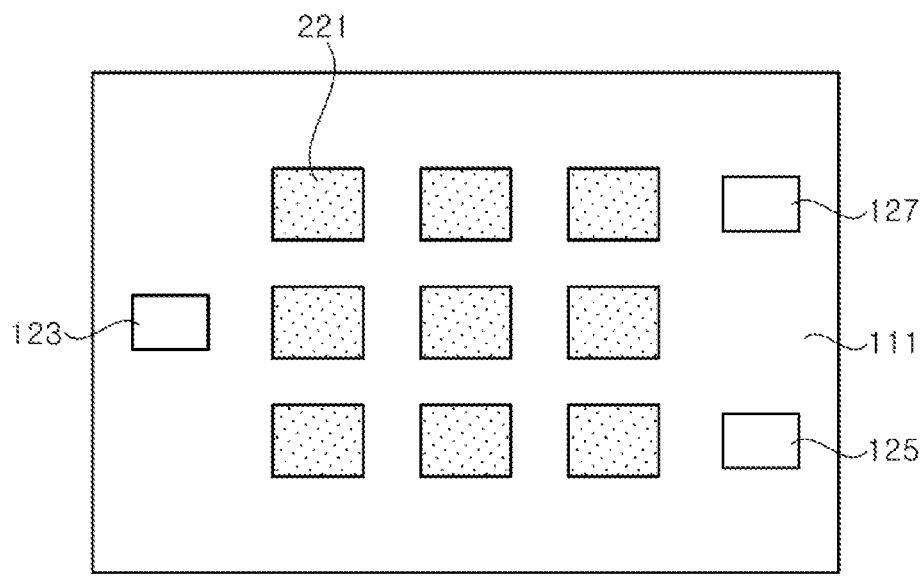
FIG. 26 is a schematic plan view of a lighting apparatus according to another exemplary embodiment.

FIG. 26 is a schematic plan view of a lighting apparatus according to another exemplary embodiment.

Referring to FIG. 26, the lighting apparatus according to the illustrated exemplary embodiment is generally similar to that described with reference to FIG. 24 and FIG. 25, except a fourth light emitting diode 127.

Since the fourth light emitting diode 127 is substantially the same as the light emitting diode 127 described with reference to FIG. 23, repeated descriptions thereof will be omitted to avoid redundancy.

Figure 27:
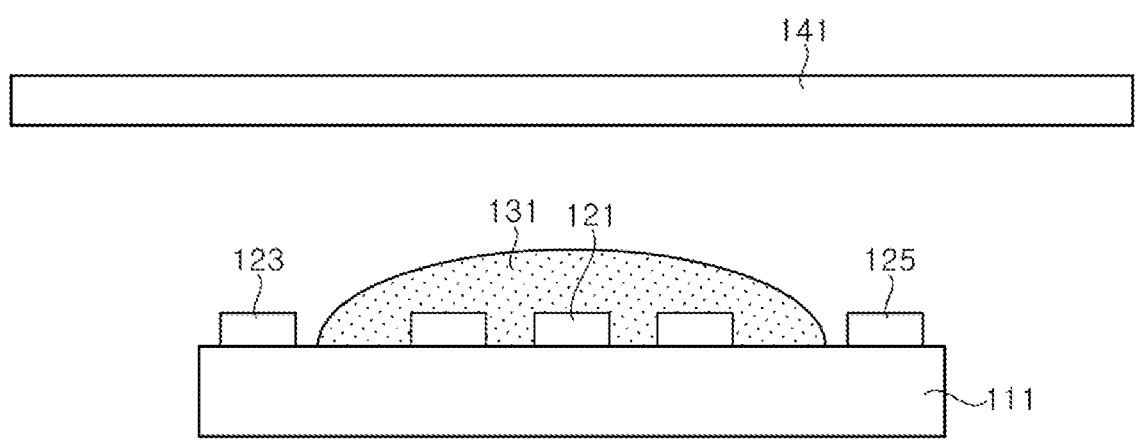
FIG. 27 is a schematic plan view of a lighting apparatus according to another exemplary embodiment.

FIG. 27 is a schematic plan view of a lighting apparatus according to another exemplary embodiment.

Referring to FIG. 27, the lighting apparatus according to the illustrated exemplary embodiment is generally similar to that described with reference to FIG. 16 and FIG. 17, except a filter 41.

The filter 41 may block unnecessary ultraviolet light emitted from the light emitting diodes 121 to the outside. For example, the filter 41 may block light in a range of about 301 nm to about 400 nm to prevent harmful effects to the human body that may be caused by ultraviolet light in this range. Light in the above range may be emitted by, for example, the first light emitting diode 121 or a wavelength converting substance. Thus, the filter 41 may be disposed outside of the wavelength converter 131. The filter 41 may include a band pass filter, without being limited thereto.

In some exemplary embodiments, a diffusion plate may be disposed instead of the filter 41 or in addition to the filter 41. The diffusion plate may mix white light generated by the first light emitting diode 121 and the wavelength converter 131 with light emitted from the second light emitting diode 123 and the third light emitting diode 125.

The filter 41 or the diffusion plate may be applied in various other exemplary embodiments described herein.

Although the light emitting unit 221 according to the illustrated exemplary embodiment is described as including the light emitting diode 121 and the wavelength converter 231, and that the light emitting diode 121 is described as being mounted directly on the circuit board 111, the light emitting unit 221 may be provided in a package form. This will be described with reference to FIG. 28.

Figure 28:
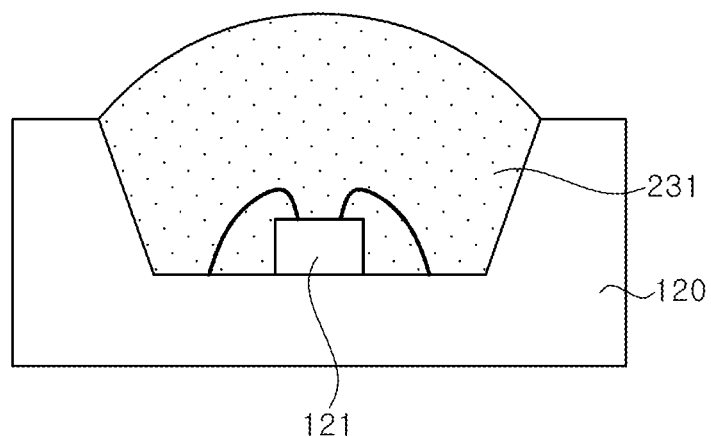
FIG. 28 is a schematic cross-sectional view of a light emitting unit according to another exemplary embodiment.

FIG. 28 is a schematic cross-sectional view of a light emitting unit according to another exemplary embodiment. FIG. 28 schematically shows a light emitting device in a package form.

Referring to FIG. 28, a light emitting unit 221 includes the light emitting diode 121 and the wavelength converter 231. The light emitting diode 121 may be mounted in a cavity of a housing 120, and the wavelength converter 231 covers the light emitting diode 121 in the cavity. The light emitting diode 121 may be electrically connected to lead electrodes through bonding wires.

The package form illustrated in FIG. 28 is merely an example, and various kinds of packages may be used. In addition, the wavelength converter 231 may cover the light emitting diode 121 in various shapes.

In the illustrated exemplary embodiment, although the light emitting unit 221 is described as being provided in the package form, at least one of the second light emitting diode 123, the third light emitting diode 24, and the fourth light emitting diode 127 may also be provided in the package form and mounted on the circuit board 111.

Figure 29:
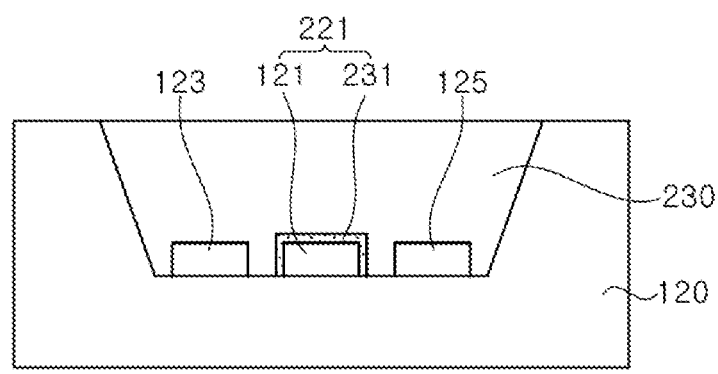
FIG. 29 is a schematic plan view illustrating a light emitting unit according to another exemplary embodiment.

FIG. 29 is a schematic plan view of a light emitting unit according to another exemplary embodiment.

Referring to FIG. 29, in the light emitting unit according to the illustrated exemplary embodiment, the first light emitting diode 121, the second light emitting diode 123, and the third light emitting diode 125 are mounted in a single package. More particularly, in the light emitting unit of FIG. 28, each light emitting diode package includes a single light emitting diode, but in the light emitting unit of FIG. 29, a light emitting diode package includes the first to third light emitting diodes 121, 123, and 125. The wavelength converter 231 may cover the first light emitting diode 121, and thus, the light emitting unit 221 may be provided in a package.

A molding member 230 may cover the light emitting unit 221, the second light emitting diode 123, and the third light emitting diode 125. The molding member 230 may be formed of, for example, a transparent resin, such as silicone resin or transparent glass. In some exemplary embodiments, the molding member 230 may include a wavelength converting substance.

According to an exemplary embodiment, the light emitting diode package including the first to third light emitting diodes 121, 123, and 125 may be mounted on the circuit board 111. In some exemplary embodiments, the light emitting diode package may further include the fourth light emitting diode 127 described above.

A plurality of light emitting diode packages may be mounted on the circuit board 111, and the light emitting diode packages may have substantially the same structure, however, the inventive concepts are not limited thereto. For example, in some exemplary embodiments, light emitting diode packages having the same multiple additional functions may be disposed on the circuit board 111, or light emitting diode packages having different additional functions may be disposed on the circuit board 111, thereby providing the lighting apparatus having multiple additional functions. In addition, although an individual LED package may implement white light, in some exemplary embodiments, white light may be implemented by a combination of a plurality of LED packages.

The lighting apparatus according to exemplary embodiments may be installed in not only an indoor living space, but also an indoor space used by a plurality of people, such as a hospital or an airport. As such, the lighting apparatus according to exemplary embodiments may be employed as a lighting system, which may provide additional functions described above along with a lighting function on a daily basis.

Although some exemplary embodiments have been described herein, it should be understood that these embodiments are provided for illustration only and are not to be construed in any way as limiting the present disclosure. It should be understood that features or components of one exemplary embodiment may also be applied to other exemplary embodiments without departing from the spirit and scope of the present disclosure.

What is claimed:

1. A lighting apparatus, comprising:
a first light emitting diode configured to emit light having a peak wavelength in a range of about 300 nm to about 470 nm;
a second light emitting diode configured to emit ultraviolet light having a peak wavelength in a range of about 286 nm to about 304 nm; and
a wavelength converter configured to convert a wavelength of light emitted from the first light emitting diode,
wherein the lighting apparatus is configured to emit white light and light that causes production of vitamin D and a cell activating substance in a human body, and
wherein the white light that the lighting apparatus is configured to emit is generated by the first light emitting diode and the wavelength converter.

2. The lighting apparatus of claim 1, wherein the first light emitting diode has a peak wavelength in a range of about 400 nm to about 420 nm.

3. The lighting apparatus of claim 1, wherein:
the wavelength converter includes a blue phosphor; and
the white light has a first peak wavelength and a second peak wavelength different from each other, the first peak wavelength is generated by the first light emitting diode, and the second peak wavelength is generated by the blue phosphor.

4. The lighting apparatus of claim 2, further comprising a plurality of light emitting units spaced apart from one another,
wherein each light emitting unit includes the first light emitting diode and the wavelength converter covering the first light emitting diode.

5. The lighting apparatus of claim 4, wherein the light emitting units are configured to emit white light having the same or different color temperatures.

6. The lighting apparatus of claim 1, wherein the wavelength converter includes a blue phosphor, a green phosphor, and a red phosphor.

7. The lighting apparatus of claim 1, wherein the ultraviolet light has a peak wavelength in a range of about 291 nm to about 301 nm.

8. The lighting apparatus of claim 7, wherein the second light emitting diode is spaced apart from the wavelength converter.

9. The lighting apparatus of claim 1, wherein the cell activating substance includes nitric oxide (NO) produced by cytochrome c oxidase activity in mitochondria.

10. The lighting apparatus of claim 9, wherein the wavelength converter includes a wavelength converting substance configured to convert incident light into light having a peak wavelength in a range of about 685 nm to about 705 nm, about 790 nm to about 840 nm, or about 875 nm to about 935 nm.

11. The lighting apparatus of claim 9, further comprising a third light emitting diode,
wherein the third light emitting diode is configured to emit light having a peak wavelength in a range of about 685 nm to about 705 nm, about 790 nm to about 840 nm, or about 875 nm to about 935 nm.

12. The lighting apparatus of claim 11, wherein an irradiance of light emitted from the wavelength converting substance is 570 W/m$^2$ or less.

13. The lighting apparatus of claim 1, further comprising a fourth light emitting diode configured to emit light that causes sterilization of pathogenic microorganisms,
wherein the fourth light emitting diode is spaced apart from the wavelength converter.

14. The lighting apparatus of claim 13, wherein the fourth light emitting diode has a peak wavelength in a range of about 400 nm to about 420 nm.

* * * * *